United States Patent [19]
Cimarusti et al.

[11] 3,971,772
[45] July 27, 1976

[54] STEROIDAL[16α,17-b]1,4-DIOXANES AND STEROIDAL[16α,17-b]1,4-DIOXINS

[75] Inventors: Christopher M. Cimarusti, Hamilton; Seymour D. Levine, North Brunswick; Frank L. Weisenborn, Titusville, all of N.J.

[73] Assignee: E. R. Squibb & Sons, Inc., Princeton, N.J.

[22] Filed: May 19, 1975

[21] Appl. No.: 578,695

Related U.S. Application Data

[63] Continuation-in-part of Ser. No. 538,978, Jan. 6, 1975, abandoned, which is a continuation-in-part of Ser. No. 433,974, Jan. 16, 1974, abandoned.

[52] U.S. Cl.................. 260/239.55 R; 260/239.57; 260/397.45
[51] Int. Cl.².......................................... C07J 5/00
[58] Field of Search.................. 260/239.55, 397.45

*Primary Examiner*—Elbert L. Roberts
*Attorney, Agent, or Firm*—Lawrence S. Levinson; Merle J. Smith; Donald J. Barrack

[57] ABSTRACT

A series of novel steroidal [[16α,17-b]1,4-dioxanes and steroidal [16α,17-b]1,4-dioxins having useful anti-inflammatory properties is disclosed herein.

36 Claims, No Drawings

STEROIDAL[16<,17-B]1,4-DIOXANES AND STEROIDAL[16<,17-B]1,4-DIOXINS

This is a continuation-in-part of copending United States patent application Ser. No. 538,978 filed Jan. 6, 1975, and now abandoned, which is a continuation-in-part of U.S. Pat. application Ser. No. 433,974 filed Jan. 16, 1974, and now abandoned.

SUMMARY OF THE INVENTION

Steroidal[16α,17-b]1,4-dioxanes and steroidal[16α,17-b]-1,4-dioxins have been prepared and found to have useful anti-inflammatory activity. The steroids encompassed by this invention are the 3,20-diketo pregnenes having an 11β-hydroxy group or an 11-keto group and having fused on the 16- and 17-positions a 1,4-dioxane ring or a 1,4-dioxin ring.

Exemplary of the steroids of the above description are steroids having the structural formula

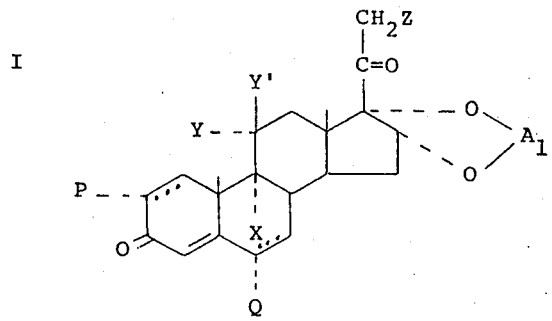

In formula I, and throughout the specification, the symbols are as defined below.

Z can be hydrogen, hydroxyl, acyloxy or halogen;
Y can be hydrogen and Y' can be hydroxyl or together Y and Y' can be =O;
X can be hydrogen or halogen;
P can be hydrogen, methyl or chloro;
Q can be hydrogen, methyl or fluoro;

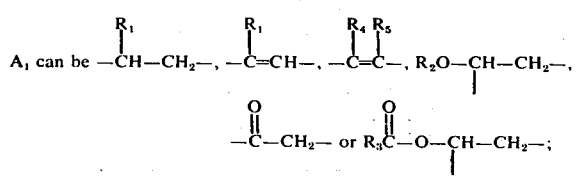

$R_1$ can be hydrogen, alkyl or aryl;
$R_2$ can be hydrogen, alkyl or arylalkyl;
$R_3$ can be alkyl, cycloalkyl or aryl; and
$R_4$ and $R_5$ can be the same or different and can be alkyl or aryl.

Steroids having the formula

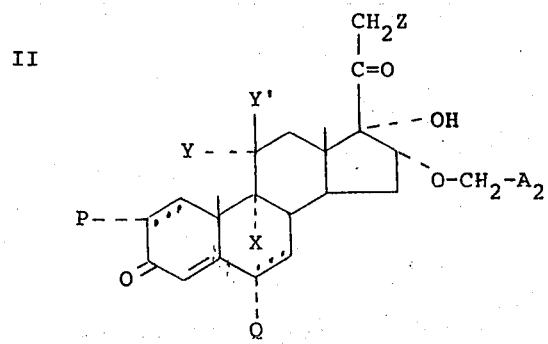

have useful anti-inflammatory activity and are useful as intermediates in the preparation of the steriodal[-16α,17-b]1,4-dioxanes and steroidal[16α,17-b]-1,4-dioxins of formula I. In formula II, and throughout the specification, the symbol $A_2$ can be

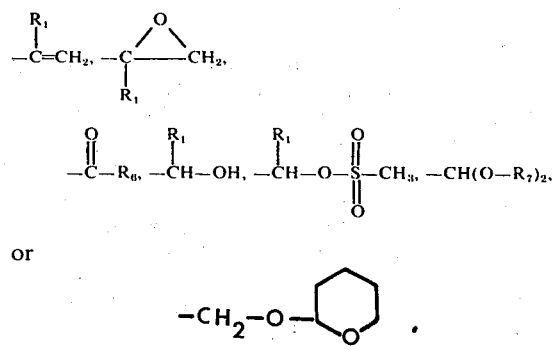

or

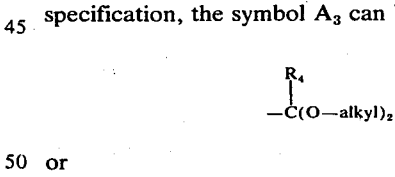

The symbol $R_6$, as used throughout the specification, can be alkyl or aryl. The symbol $R_7$, as used throughout the specification, can be alkyl or arylalkyl.

Steroids having the formula

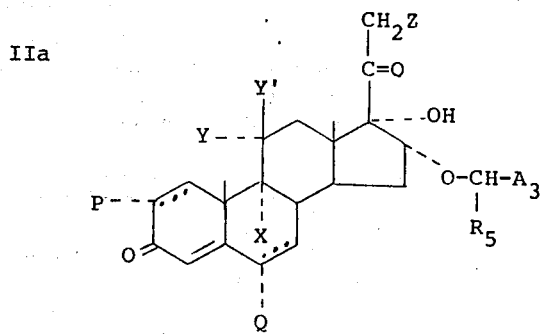

also have useful anti-inflammatory activity and are useful as intermediates in the preparation of the novel steroids of formula I. In formula IIa, and throughout the specification, the symbol $A_3$ can be $$-\overset{R_4}{\underset{|}{C}}(O-\text{alkyl})_2$$

or $$-\overset{O}{\underset{\|}{C}}-R_4.$$

The dotted lines in the 1,2- and the 6,7-positions of the steroids of this invention represent the optional presence of double bonds.

The term "pregnene", as used throughout the specification, refers to pregnanes having ethylenic unsaturation in one or more positions. Exemplary of pregnanes specifically contemplated are $\Delta^4$-pregnenes, $\Delta^{1,4}$-pregnadienes, $\Delta^{4,6}$-pregnadienes, and $\Delta^{1,4,6}$-pregnatrienes. The $\Delta^4$-pregnenes and the $\Delta^{1,4}$-pregnadienes are preferred.

The expression "1,4-dioxane ring", as used throughout the specification, refers to unsubstituted and substituted 1,4-dioxane rings. Exemplary substituents are alkyl, arylalkyl, aryl, alkoxy, arylalkoxy,

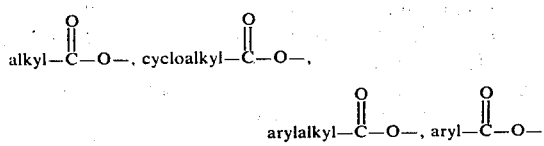

and oxo groups.

The expression "1,4-dioxin ring", as used throughout the specification, refers to unsubstituted and substituted 1,4-dioxin rings. Exemplary substituents are alkyl, arylalkyl, and aryl groups.

The term "alkyl", as used throughout the specification, refers to both branched and straight chain alkyl groups having 1 to 8 carbon atoms. Alkyl groups of 1 to 4 carbon atoms are preferred, and methyl is the most preferred.

The term "cycloalkyl", as used throughout the specification, refers to cycloalkyl groups having 3 to 6 carbon atoms.

The term "aryl", as used throughout the specification, refers to phenyl or phenyl substituted with one or more halogen, alkyl, and alkoxy groups. Phenyl and monosubstituted phenyl are the preferred aryl groups.

The term "halogen", as used throughout the specification, refers to fluorine, chlorine, bromine, and iodine.

The term "alkoxy", as used throughout the specification, refers to groups having the structure alkyl-0- wherein alkyl is as defined above. Alkoxy groups having 1 to 4 carbon atoms are preferred, and methoxy is the most preferred.

The term "acyloxy", as used throughout the specification, refers to groups wherein the acyl portion is a physiologically acceptable acid residue derived from an organic or inorganic acid. Exemplary monocarboxylic acids, are those having the formula R-COOH wherein R is alkyl, cycloalkyl, arylalkyl or aryl; e.g., acetic, propionic, valeric, cyclohexanecarboxylic, phenylacetic, benzoic, and toluic acids. Exemplary polycarboxylic acids are malonic, succinic, glutaric, adipic, pimelic, and phthalic acids. Exemplary inorganic acid are sulfuric, nitric, and phosphoric acids.

DETAILED DESCRIPTION OF THE INVENTION

The steroids of formulas I, II and IIa are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion. The topical mode of administration is preferred.

Cycloborate esters of 16α,17-dihydroxy steroids having the formula

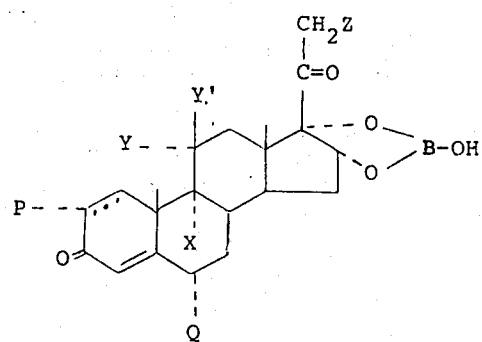

are one of the starting materials for the preparation of the steroids of formula I. The cycloborate esters of formula III are known; see, for example, United States patent 2,831,003, issued Apr. 15, 1958. They can be prepared by reacting the corresponding 16α,17-dihydroxy steroid with boric acid anhydride in an organic solvent at reflux temperature.

Exemplary cycloborate ester starting materials of formula III are

11β,16α,17,21-tetrahydroxypregn-4-ene-3,20-dione, 16,17-cycloborate, 9-fluoro-11β,16α,17,21-tetrahydroxypregn-4-ene-3,20-dione, 16,17-cycloborate, 6α,9-difluoro-11β,16α,17,21-tetrahydroxypregn-4-ene-3,20-dione, 16,17-cycloborate, 11β,16α,17,21-tetrahydroxy-6α-methylpregn-4-ene-3,20-dione, 16,17-cycloborate, 21-chloro-11β,16α,17-trihydroxypregn-4-ene-3,20-dione, 16,17-cycloborate, 21-chloro-9-fluoro-11β,16α,17-trihydroxypregn-4-ene-3,20-dione, 16,17-cycloborate, 21-chloro-6α,9-difluoro-11β,16α,17-trihydroxypregn-4-ene-3,20-dione, 16,17-cycloborate, 21-chloro-6α-fluoro-11β,16α,17-trihydroxypregn-4-ene-3,20-dione, 16,17-cycloborate, 21-chloro-11β,16α,17-trihydroxy-6α-methylpregn-4-ene-3,20-dione, 16,17-cycloborate, 11β,16α,17,21-tetrahydroxypregna-1,4-diene-3,20-dione, 16,17-cycloborate, 9-fluoro-11β,16α,17,21-tetrahydroxypregna-1,4-diene-3,20-dione, 16,17-cycloborate, 6α,9-difluoro-11β,16α,17,21-tetrahydroxypregna-1,4-diene-3,20-dione, 16,17-cycloborate, 6α-fluoro-11β,16α,17,21-tetrahydroxypregna-1,4-diene-3,20-dione, 16,17-cycloborate, 11β,16α,17,21-tetrahydroxy-6α-methylpregna-1,4-diene-3,20-dione, 16,17-cycloborate, 21-chloro-11β,16α,17-trihydroxypregna-1,4-diene-3,20-dione, 16,17-cycloborate, 21-chloro-9-fluoro-11β,16α,17-trihydroxypregna-1,4-diene-3,20-dione, 16,17-cycloborate, 21-chloro-6α,9-difluoro-11β,16α,17-trihydroxypregna-1,4-diene-3,20-dione, 16,17-cycloborate, 21-chloro-6α-fluoro-11β,16α,17-trihydroxypregna-1,4-diene-3,20-dione, 16,17-cycloborate, 21-chloro-11β,16α,17-trihydroxy-6α-methylpregna-1,4-diene-3,20-dione, 16,17-cycloborate, 2-chloro-11β,16α,17,21-tetrahydroxypregna-1,4-diene-3,20-dione, 16,17-cycloborate, 2-chloro-9-fluoro-11β,16α,17,21-tetrahydroxypregna-1,4-diene-3,20-dione, 16,17-cycloborate, 9-fluoro-11β,16α,17,21-tetrahydroxypregna-1,4,6-triene-3,20-dione, 16,17-cycloborate.

Diazoalkenes having the formula

IV are also used as starting materials for the preparation of the steroids of formula I wherein $A_1$ is

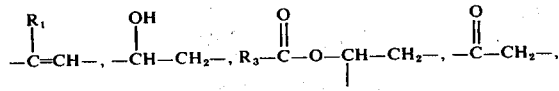

In formula IV, those diazoalkenes wherein $R_1$ is hydrogen or alkyl are known; see, for example, the *Journal of the American Chemical Society*, 91, 711 (1969). The preparation of the diazoalkene of formula IV wherein $R_1$ is aryl (e.g., 2-phenyl-3-diazo-1-propene) is described in the examples of this specification.

Reaction of a cycloborate ester of formula III with a diazoalkene of formula IV yields a steroid having the formula V
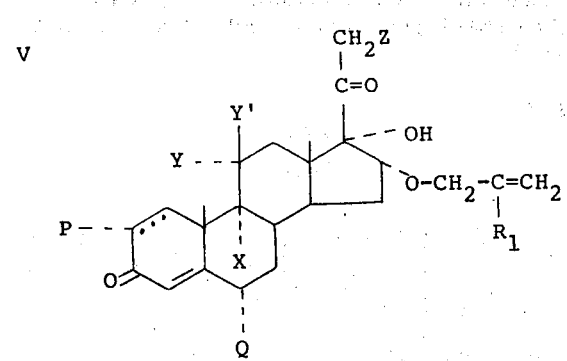

The reaction can be conducted in an organic solvent, preferably a lower alkanol such as methanol, at a temperature of about −10°C to +40°C for about 30 minutes to 4 hours, preferably at 0°C to 20°C for 30 minutes to 1 hour. The steroid and the diazoalkene are reacted in at least a 1:4 molar ratio.

The steroid of formula V, wherein Z is other than hydroxyl, can be reacted with m-chloroperbenzoic acid to yield a steroid having the formula VI
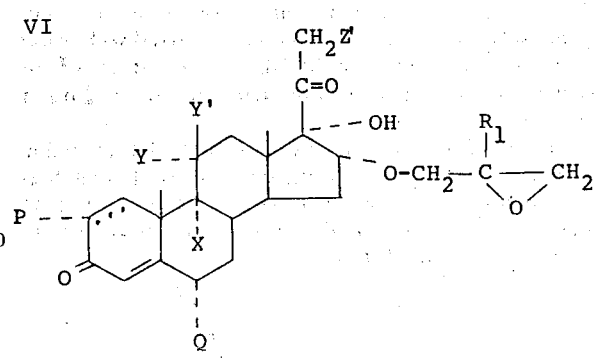

In formula VI, and throughout the specification, Z' can be hydrogen, acyloxy or halogen. The reaction can be conducted in an organic solvent, preferably a halogenated hydrocarbon such as dichloromethane, at a temperature of from about 0°C to 40°C for about 1 hour to 96 hours, preferably at room terperature for about 2 hours to 72 hours. The steroid of formula V and the m-chloroperbenzoic are reacted in approximately a 1:1 molar ratio.

Reaction of a steroid of formula VI when $R_1$ is alkyl or aryl with a strong oxidizing agent such as periodic acid, yields a steroid having the formula VII
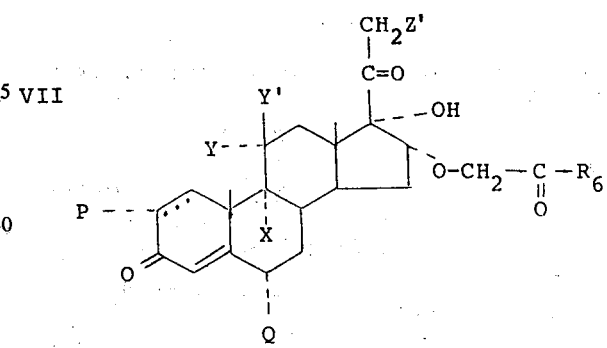

Reaction of a steroid of formula VI when $R_1$ is hydrogen with a strong oxidizing agent yields a cyclic lactol (formula VIII) which is in equilibrium with the corresponding aldehyde (formula VIIIa), i.e.,

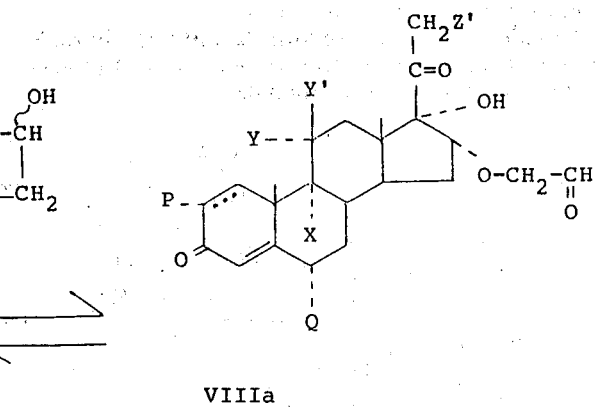

VIII                    VIIIa

These oxidation reactions can be conducted in an organic solvent such as tetrahydrofuran mixed with water at a temperature of about 0°C to 40°C, for about 1 hour to 8 hours, preferably at room temperature for 2 hours to 4 hours.

The steroids of formula VII or VIII can be reacted in a slurry or solution of an organic acid catalyst such as p-toluenesulfonic acid in an organic solvent such as benzene to yield steroidal 2′,3′-dihydro[16α,17-b]1,4-dioxins having the formula IX
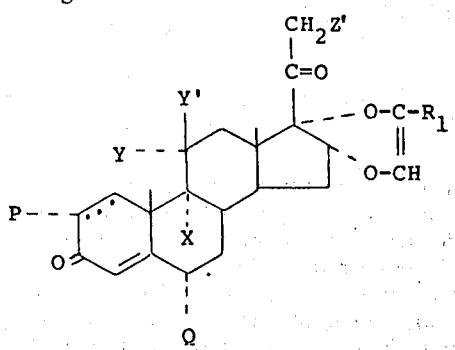

The reaction can be conducted under reflux conditions in an inert atmosphere for about 2 hours to 48 hours, preferably 4 hours to 24 hours.

Reaction of a steroid of formula VIII with an anhydride having the formula

yields a steroidal [16α,17-b]1,4-dioxane having the formula

X
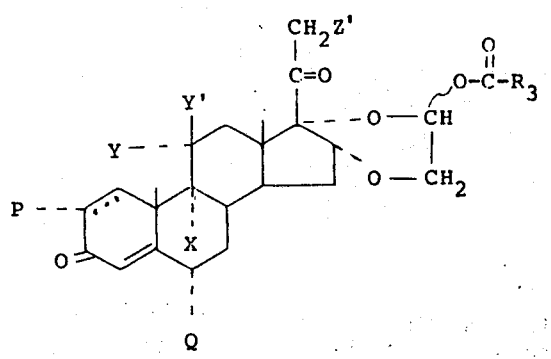

The reaction can be conducted in an organic solvent such as pyridine at a temperature of about 0°C to 40°C for about 30 minutes to 4 hours, preferably at room temperature for 1 hour to 2 hours.

Oxidation of a steroid of formula VIII with Fetizon's reagent (*Angew. Chem. Internat. Edit.*, 8, 444 (1969) yields a steroid having the formula XI
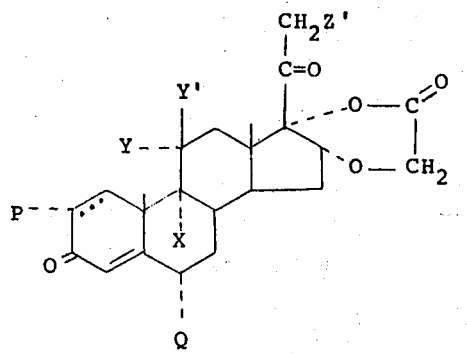

The reaction can be conducted in an organic solvent such as benzene, toluene, etc. at a temperature of about 80 C to 110 C for about 2 hours to 48 hours, preferably at reflux temperature for about 24 hours.

Reaction of a steroid of formula VII or VIII with sodium borohydride yields a steroid having the formula XII
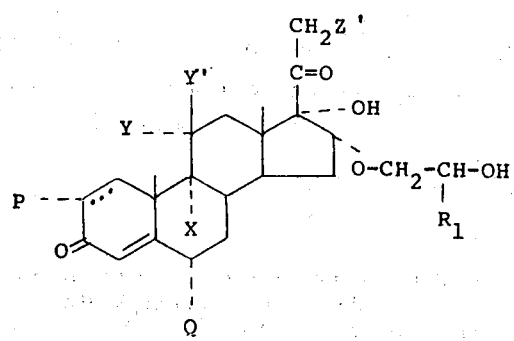

The reaction can be carried out in an organic solvent, preferably a lower alkanol such as methanol at a temperature of from about 10 C to 20 C for about 10 to 60 minutes, preferably at about 0 C for 10 minutes to 30 minutes.

A 16-hydroxyethoxy steroid of formula XII can be reacted with a methanesulfonyl halide (methanesulfonyl chloride is preferred) to yield a steroid having the formula XIII
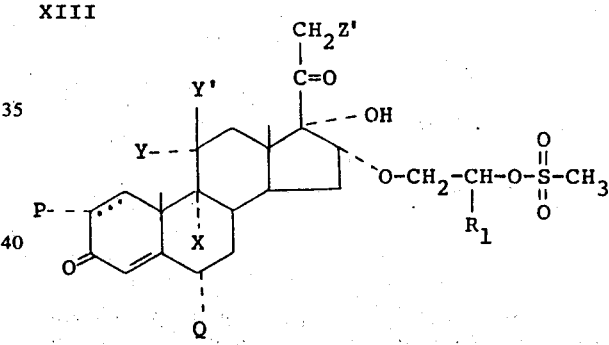

The reaction can be carried out in an organic solvent such as pyridine, in an inert atmosphere, at a temperature of about 10 C to 40 C for 30 minutes to 4 hours, preferably at about 0 C for 1 hour to 2 hours.

Reaction of a steroid of formula XIII with sodium bicarbonate in a dipolar aprotic solvent such as dimethylsulfoxide yields a steroidal[16 ,17-b]1,4-dioxane having the formula XIV
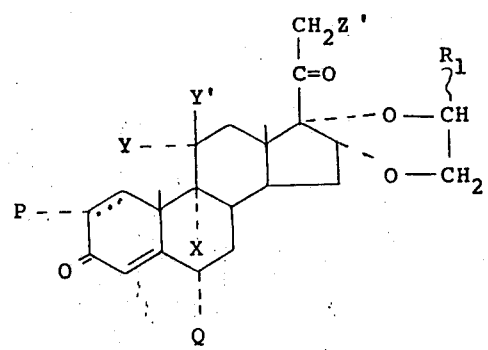

The reaction can be conducted at a temperature of from about 60 C to 130 C for about 1 hour to 24 hours, preferably at about 110 C for 2 hours to 4 hours.

The 21-hydroxyl analogs of the steroids of formulas VI, VII, VIII, VIII*a* IX, X, XI, XII, XIII, and XIV are readily obtainable by saponification of the corresponding 21-acyloxy steroids.

Steroidal[16α, 17-b]1,4-dioxanes of formula I wherein A₁ is

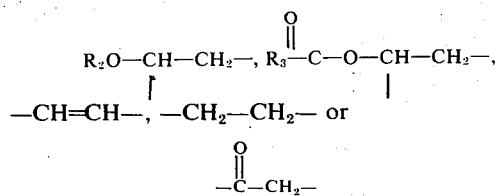

can be prepared from the cycloborate esters of 16α,17-dihydroxy steroids of formula III and diazoethers having the formula

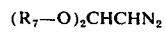

The diazoethers of formula XV are known; for example, *Chem. Ber.* 100, 1491 (1967).

Reaction of a cycloborate ester of formula III with a diazoether of formula XV yields a steroid having the formula

XVI

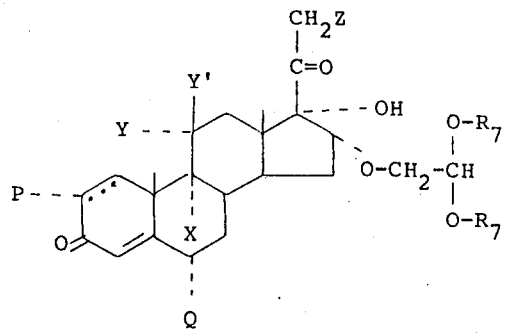

The reaction can be conducted in an organic solvent, preferably a lower alkanol such as methanol, at a temperature of from about −10°C to 40°C until nitrogen evolution ceases. The preferred reaction temperature is from 0°C to 20°C.

The steroid of formula XVI can be reacted with an organic acid such as p-toluenesulfonic acid in an organic solvent such as benzene to yield a steroidal[-16α,17-b]1,4-dioxane having the formula

XVII

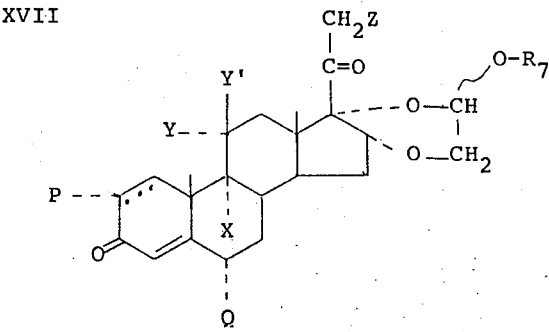

The reaction can be carried out at a temperature of about 60°C to 140°C for about 1 hour to 24 hours, preferably 80°C to 110°C for 2 hours to 4 hours.

Reaction of a steroid of formula XVI with a mineral acid, e.g., hydrochloric acid, yields a steroidal[16α,17-b]-1,4-dioxane of formula VIII. The reaction can be carried out in an organic solvent such as tetrahydrofuran at a temperature of from about 0°C to 100°C for about 1 hour to 24 hours, preferably 40°C to 60°C for 2 hours to 8 hours.

A steroid of formula VIII can be used to obtain a steroid of formula IX (wherein R₁ is hydrogen), a steroid of formula X, a steroid of formula XI and a steroid of formula XIV (wherein R₁ is hydrogen) following the procedures set forth above.

Steroidal[16α,17-b]1,4-dioxanes of formula I wherein A₁ is —CH₂—CH₂— can also be prepared from the cycloborate esters of 16α,17-dihydroxy steroids of formula III and 2-(tetrahydropyran-2-yloxy)-1-diazoethane, the preparation of which is set forth in the examples below.

Reaction of a cycloborate ester of formula III with 2-(tetrahydropyran-2-yloxy)-1-diazoethane yields a steroid having the formula

XVIII

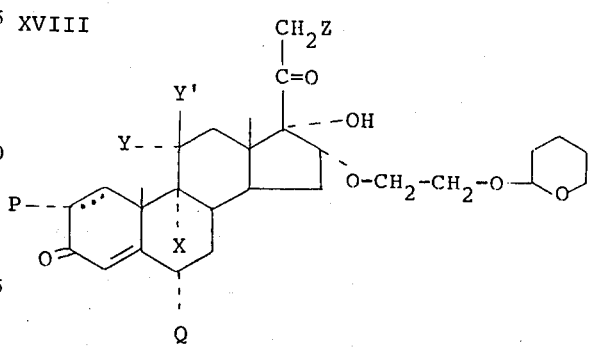

The reaction can be carried out in organic solvent, preferably a lower alkanol such as methanol, at a temperature of from about −10°C to 40°C, preferably 0°C to 20°C. The reaction is continued until nitrogren evolution ceases.

A steriod of formula XVIII may be cleaved with an acid to yield a steriod of formula XII (wherein R₁ is hydrogen. The cleavage reaction can be conducted in water at a temperature of from about 0°C to 40°C, preferably at room temperature, for about 1 hour to 24 hours, preferably 2 hours to 8 hours. Both organic and inorganic acids can be used in this reaction. The preparation of a steriod of formula I wherein A₁ is —CH₂—CH₂— from a steriod of formula XII is set forth above.

A steriod of formula I wherein A₁ is

can be prepared from the cycloborate esters of 16α,17-dihydroxy steriods of formula III and diazoethers having the formula

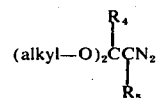   XIX.

Reaction of a cycloborate ester of formula III with a diazoether of formula XIX yields a steriod having the formula

XX

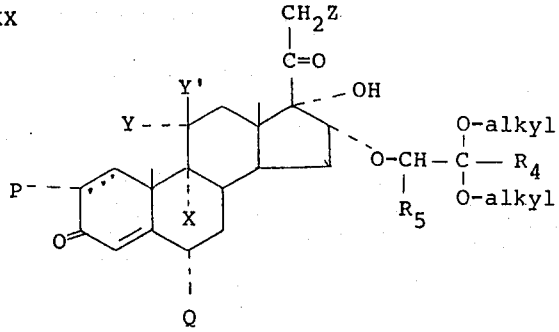

The reaction can be conducted in an organic solvent, preferably a lower alkanol such as methanol, at a temperature of from about −10°C to 40°C until nitrogen evolution ceases. The preferred reaction temperature is from 0°C to 20°C.

Reaction of a steriod of formula XX with a mineral acid, e.g. hydrochloric acid, yields a steriod having the structure

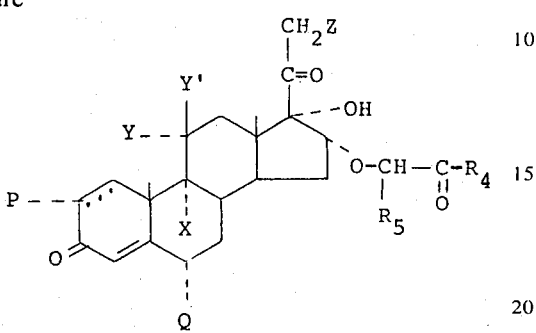

XXI

The reaction can be carried out in an organic solvent such as tetrahydrofuran at a temperature of from about 0°C to 100°C for about 1 hour to 24 hours, preferably 40°C to 60°C for 2 hours to 8 hours.

A steriod of formula XXI, wherein Z is other than hydroxyl, can be reacted with a slurry or solution of organic acid such as p-toluenesulfonic acid in an organic solvent such as benzene to yield a steriod having the formula

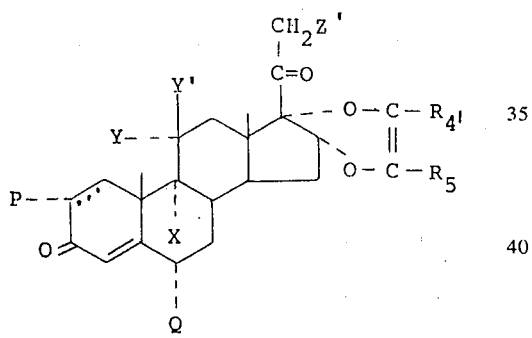

XXII

The reaction can be conducted under reflux conditions in an inert atmosphere for about 2 hours to 48 hours, preferably 4 hours to 24 hours.

The 21-hydroxyl analogs of the steriods of formula XXII are readily obtainable by saponification of the corresponding 21-acyloxy steriod.

Those steriods of formula I containing ethylenic unsaturation in the 6,7-position can be prepared as described above with the additional step of selectively introducing a carbon-carbon double bond in the 6,7-position of either a steriod starting material of formula III or a steriod product of formula VIII, IX, X, XI, XIV, XVII, or XXII without effecting other functional groups of the steriod. Exemplary of the oxidizing agents which meet the above requirements is 2,3-dichloro-5,6-dicyano-1,4-benzoquinone when used in the presence of an acid. About one molar equivalent of the oxidizing agent is used per molar equivalent of steriod. The oxidation reaction can be conducted in an organic solvent such as benzene, toluene, dioxane, etc.; dioxane is preferred. The reaction can be carried out for about 1 hour to 96 hours at a temperature of about 50°C to 150°C, preferably for about 4 to 24 hours at about 70°C to 130°C. Alternately a borate containing unsaturation in the 6,7-position can be prepared from the corresponding, known 6,7 -unsaturated 16,17-diols and boric anhydride.

Additional methods for the preparation of the compounds of this invention will be readily apparent to a person of ordinary skill in the steriod art. For example, those steriods of this invention having a halogen in the 21-position can be prepared from the corresponding 21-hydroxy steriod by reacting the later with an alkyl or aryl sulfonyl halide (e.g., methanesulfonyl chloride or p-toluenesulfonyl chloride), in the presence of an organic base such as pyridine, to yield a 21-alkyl (or aryl) sulfonyloxy steriod. The 21-alkyl (or aryl) sulfonyloxy steroid intermediate can be reacted with alkali metal halide (e.g., potassium fluoride, lithium chloride, lithium bromide, sodium iodide, etc.) to yield the corresponding 21-halo steriod.

It will also be readily apparent to the practitioner of this invention that because of the stability of the dioxane and dioxin ring structures, functional groups represented by the various symbols used in formula I can be added to the steriod nucleus after the addition of the dioxane or dioxin ring.

Using procedures well known to those of ordinary skill in the steriod art it is also possible to prepare 21-acyloxy steriods of this invention from the corresponding 21-hydroxy steriods. Other variations will be apparent to the practitioner of this invention.

Steroids of formula I wherein P and Q are hydrogen are preferred.

Steroids of formula I wherein X is halogen are preferred, and those wherein X is fluorine are most preferred.

Steroids of formula I wherein Y is hydrogen and Y' is hydroxyl are preferred.

Steroids of formula I wherein $A_1$ is $-CH_2-CH_2-$,

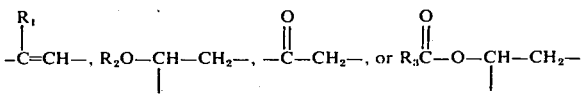

are preferred.

Steroids of formula I wherein Z is hydrogen, hydroxyl,

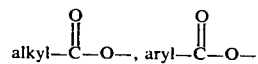

or halogen are preferred.

The following examples are specific embodiments of this invention.

EXAMPLE 1

9-Fluoro-5'ξ,11β,21-trihydroxypregn-4-eno[16α,17-b]-[1,4]dioxane-3,20-dione, 21-acetate

A.

16α-Allyloxy-9-fluoro-11β,17,21-trihydroxypregn-4-ene-3,20-dione 6.6 g of 9-fluoro-11β,16α,17,21-tetrahydroxypregn-4-ene-3,20-dione,16,17-cycloborate is added to a solution of vinyl diazomethane in 1:1 methanol-ether at 0°C. After stirring for 1 hour, the solvent is evaporated and the residue dissolved in chloroform and chromatographed on a 150-g silica gel column. Elution with 5% ethyl acetate in chloroform gives 1.04 g of TLC (thin layer chromatography) pure material. Two recrystallizations from acetone-hexane give 0.5 of 16α-allyloxy-9-fluoro-11β,17,21-trihydroxypregn-4-ene-3,20-dione, melting point 199°–201°C.

Anal. Calc'd for $C_{24}H_{33}FO_6$: C,66.04; H, 7.62; F, 4.35. Found: C, 65.82; H, 7.83; F, 4.24.

B.
16α-Allyloxy-9-fluoro-11β,17,21-trihydroxypregn-4-ene-3,20-dione, 21-acetate A solution of 2.5 g of 16α-allyloxy-9-fluoro-11β,17,21-trihydroxypregn-4-ene- 3,20-dione in 25 ml of pyridine is stirred for 2 hours with 2.5 ml of acetic anhydride and the solvent is then removed in vacuo. A solution of the residue in chloroform is washed with 5% hydrochloric acid, water, 10% sodium bicarbonate solution, water, and dried. Solvent removal in vacuo gives an oil which crystallizes from acetone-hexane to yield 2.5 g of 16α-allyloxy-9-fluoro-11β,17,21-trihydroxypregn-4-ene-3,20-dione, 21-acetate, melting point 189°–191°C.

C.
9-Fluoro-11β,17,21-trihydroxy-16α-(oxiranyl-methoxy)-pregn-4-ene-3,20-dione, 21-acetate A solution of 6.44 g of 9-fluoro-16α-allyloxy-11β,17,21-trihydroxypregn-4-ene-3,20-dione, 21-acetate in 150 ml of dichloromethane is stirred with 2.88 g of m-chloroperbenzoic acid for 19 hours at room temperature. The resulting solution is washed with a mixture of 10% potassium carbonate solution and 10% sodium sulfite solution, dried, and evaporated in vacuo. The residue is dissolved in dichloroemthane and chromatographed on a 125 g - silica gel column. Elution with chloroform and a chloroform-ethyl acetate mixture gives 3.5 g of unreacted starting material in fractions (100 ml) 25–37 and 1.7 g (25.6%) of TLC pure product in fractions 49–61.

The 1.7 g is recrystallized from acetone-hexane to give 991 mg of material having a melting point of 191°–192.5°C. A 500 mg portion of this material is recrystallized from the same solvent to give 430 mg of 9-fluoro-11β,17,21-trihydroxy-16α-(oxiranyl-methoxy)pregn-4-ene-3,20-dione, 21-acetate, melting point 191°–192.5°C.

Anal. Calc'd for $C_{26}H_{35}FO_8$: C, 63.15; H, 7.13; F, 3.84. Found: C, 63.17; H, 6.84; F, 3.64.

D.
9-Fluoro-5'ξ,11β,21-trihydroxypregn-4-eno[16α,17-b]-[1,4]dioxane-3,20-dione, 21-acetate A solution of 20.1 g of crude 9-fluoro-11β,17,21-trihydroxy-16α-(oxiranyl-methoxy)pregn-4-ene-3,20-dione, 21-acetate in 300 ml of tetrahydrofuran is stirred with a solution of 30 g of periodic acid in 75 ml of water for 6¾ hours. The solution is diluted with water and extracted with chloroform. The chloroform extract was washed with 5% sodium bicarbonate solution, dried, and evaporated in vacuo to give 18.2 g of crude product. This material is dissolved in 60 ml of dichloromethane and chromatographed on a 450 g -silica gel column. Fractions of 250 ml are collected as the column is eluted with 3 liters of dichloromethane, 3 liters of chloroform, and then 3 liters of 19:1 chloroform-ethyl acetate. Fractions 17–21 are combined and evaporated in vacuo to give 4.4 g of 9-fluoro-16α-allyloxy-11β,17,21-trihydroxypregn-4-ene-3,20-dione, 21-acetate.

Fractions 23–31 are combined and evaporated in vacuo to give 8.1 g of slightly impure (53.2% based on recovered material) 9-fluoro-5'ξ, 11β, 21-trihydroxypregn-4-eno[16α,-17-b][1,4]dioxane-3,20-dione, 21-acetate. A portion of this material is recrystallized from acetone-hexane and then from acetonitrile to give the analytical sample, melting point 205°–208°C.

Anal. Calc'd for $C_{25}H_{33}FO_8$: C, 62.10; H, 7.50; F, 3.93.

Found: C, 62.22; H, 7.28; F, 3.69.

EXAMPLE 2
9-Fluoro-2',3'-dihydro-11β, 21-dihydroxy-5'-methyl-pregn-4-eno[16α,17-b][1,4]dioxin-3,20-dione, 21-acetate

A.
9-Fluoro-11β,17,21-trihydroxy-16α-[(2-methyl-2-propenyl)oxy]pregn-4-ene-3,20-dione A solution of 2-methyl-3-diazo-1-propene in 250 ml of ether (prepared from 0.2 mole of N-(2-methyl-2-propenyl)-ethyl carbamate by the method of J. L. Brewbaker and H. Hart, *J. Am. Chem. Soc.*, 91, 711 (1969) ) is diluted with 300 ml of methanol and cooled to 0°C. A total of 6.5 g of 9-fluoro-11β16α, 17,21,-tetrahydroxypregn-4-ene-3,20-dione, 16,17-cycloborate is added in portions until the initial red color fades and nitrogen evolution ceases. The solvent is evaporated in vacuo and the residue dissolved in chloroform and chromatographed on a 100 g — silica gel column. Elution with chloroform and chloroform-ethyl acetate gives TLC homogeneous material which crystallizes from acetone-hexane to give 3.73 g of 9-fluoro-11β,17,21-trihydroxy-16α-[(2-methyl-2-propenyl)oxy]pregn-4-ene-3,20-dione, melting point 213°–215°C, softening at 198°–200°C.

Anal. Calc'd for $C_{25}H_{35}FO_6$: C, 66.64; H, 7.83; F, 4.22.

Found: C, 66.41; H, 8.03; F, 4.16.

B.
9-Fluoro-11β,17,21-trihydroxy-16α-[(2-methyl-2-propenyl)oxy]pregn-4-ene-3,20-dione,21acetate A solution of 3 g of 9-fluoro-11β,17,21-trihydroxy-16α-[(2-methyl-2-propenyl)oxy]pregn-4-ene-3,20-dione in 25 ml of pyridine is stirred for 2 hours with 4 ml of acetic anhydride. The solvent is removed in vacuo and the residue is dissolved in chloroform, washed with 5% hydrochloric acid solution, water, 5% sodium bicarbonate solution, and dried. Solvent removal in vacuo gives a solid which is recrystallized from acetone-hexane to give 2.82 g of material having a melting point of 230°–231°C. Recrystallization of 0.6 g of this material from acetone-hexane gives 481 mg of 9-fluoro-11β,17,21-trihydroxy-16α-[(2-methyl-2-propenyl)-oxy]pregn-4-ene-3,20-dione, 21-acetate, melting point 230°–232°C.

Anal. Calc'd for $C_{27}H_{37}FO_7$: C, 65.84; H, 7.57; F, 3.86.

Found: C, 65.89; H, 7.56; F, 4.06.

C.
9-Fluoro-11β,17,21-trihydroxy-16α-[(2-methyloxiranyl)methoxy]pregn-4-ene-3,20-dione, 21-acetate A slurry of 1.0 g of 9-fluoro-11β,17,21-trihydroxy-16α-[(2-methyl-2-propenyl)oxy]pregn-4-ene-3,20-dione, 21-acetate in 50 ml of dichloromethane is stirred with 500 mg of m-chloroperbenzoic acid at room temperature for 210 minutes. The resulting solution is washed with a mixture of 10% sodium carbonate solution and 10% sodium sulfite solution, dried, and evaporated to give 1.04 g of oil which solidifies. Recrystallization from acetone-hexane gives 793 mg of material, melting point 221°–224°C and 160 mg of material, melting point 219°–224°C. Recrystallization of a mixture of 390 mg of crop 1 and 160 mg of crop 2 from acetone-hexane gives 298 mg of 9-fluoro-11β,17,21-trihydroxy-16α-[(2-methyl-oxiranyl)methoxy]pregn-4-ene-3,20-dione, 21-acetate, melting point 223°–227°C.

Anal. Calc'd for $C_{27}H_{37}FO_7$: C, 63.76; H, 7.33; F, 3.74. Found: C, 63.96; H, 7.10; F, 3.93.

The nmr spectrum of this material indicates it is a mixture of epimers (ca. 2:1 ratio) at the quaternary epoxide carbon atom.

D.
9-Fluoro-11β,17,21-trihydroxy-16α-(2-oxopropoxy)-pregn-4-ene-3,20-dione, 21-acetate A solution of 1.54 g of 9-fluoro-11β,17,21-trihydroxy-16α-[(2-methyl-oxiranyl)methoxy]pregn-4-ene-3,20-dione, 21-acetate in 50 ml of tetrahydrofuran is stirred for 270 minutes with a solution of 2.6 g of periodic acid in 20 ml of water. The solution is poured into water and extracted with chloroform. The chloroform solution is washed with 10% sodium bicarbonate solution, dried, and evaporated in vacuo to give an oily residue. This is dissolved in chloroform and chromatographed on a 40-silica gel column. Elution with chloroform gives 400 mg of slightly impure product followed by 990 mg of TLC homogeneous solid. The 900 mg is recrystallized twice from acetone-hexane to give 328 mg of 9-fluoro-11β,17,21-trihydroxy-16α-(2-oxopropoxy)pregn-4-ene-3,20-dione, 21-acetate, melting point 203°–208°C.

Anal. Calc'd for $C_{26}H_{35}FO_8$: C, 63.15; H, 7.13; F, 3.84. Found: C, 63.01; H, 7.04; F, 4.08.

E.
9-Fluoro-2',3'-dihydro-11β,21-dihydroxy-5'-methyl-pregn-4-eno[16α,17-b][1,4]dioxin-3,20-dione, 21-acetate A slurry of 100 mg of p-toluenesulfonic acid in 250 ml of benzene is refluxed with a Dean-Stark trap. The first 50 ml of benzene-water azeotrope is discarded and Linde type 4A molecular sieves are added to the trap. After 30 minutes at reflux, the solution is cooled and 1.0 g of 9-fluoro-11β,17,21-trihydroxy-16α-(2-oxopropoxy)pregn-4-ene-3,20-dione, 21-acetate is added. The resulting slurry is refluxed for 5 hours under nitrogen, cooled, diluted with chloroform, washed with 5% sodium bicarbonate solution, water, dried and evaporated. The crude residue is dissolved in a small amount of chloroform and chromatographed on a 20 g — silica gel column. Elution with chloroform gives 805 mg of material which is recrystallized from acetone-hexane to give 501 mg of 9-fluoro-2',3'-dihydro-11β,21-dihydroxy-5'-methylpregn-4-eno[16α,17-b][1,4]-dioxin-3,20-dione, 21-acetate, melting point 233°–235°C, dec.

Anal. Calc'd for $C_{26}H_{33}FO_7$: C, 65.53; H, 6.98; F, 3.99. Found: C, 65.78; H, 6.84; F, 4.14.

EXAMPLE 3
9-Fluoro-2',3'-dihydro-11β,21-dihydroxy-5'-methyl-pregn-4-eno[16α,17-b][16α,17-b][1,4]dioxin-3,20-dione A solution of 886 mg of 9-fluoro-2',3'-dihydro-11β,21-dihydroxy-5'-methylpregn-4-eno[16α,17-b][1,4]dioxin-3,20-dione, 21-acetate (prepared as described in Example 2) in 270 ml of methanol is cooled to 0°C and 27 ml of 10% potassium carbonate solution is added. After 15 minutes, 27 ml of acetic acid is added and the mixture is diluted with water and extracted with chloroform to give 775 mg of TLC pure 9-fluoro-2',3'-dihydro-11β,21-dihydroxy-5'-methyl-pregn-4-eno[16α,17-b][1,4]dioxin-3,20-dione.

EXAMPLE 4
9-Fluoro-2',3'-dihydro-11β,21-dihydroxy-P5'-phenyl-pregn-4-eno[16α,17-b][1,4]dioxin-3,20-dione, 21-acetate

A.
9-Fluoro-11β,17,21-trihydroxy-16α-[(2-phenyl-2-propenyl)oxy]pregn-4-ene-3,20-dione, 21-acetate a. N-(2-propenyl)phthalimide A mixture of 60 g of potassium phthalimide and 66.4 g of α-bromomethyl styrene (prepared by the method of S. F. Reed, Jr., J. Org. Chem., 30, 3258 (1965)) in 150 ml of dimethylformamide is refluxed for 2 hours, cooled, and diluted with 400 ml of water. The resulting solid is filtered and dried in vacuo to give 83.4 g of N-(2-phenyl-2-propenyl)phthalimide. A small sample that is recrystallized from acetone-hexane has a melting point of 118°–121°C.

b. N-(2-phenyl-2-propenyl)ethyl carbamate

A solution of 83 g of N-(2-phenyl-2-propenyl) phthalimide and 30 g of 99% hydrazine-hydrate is refluxed for 270 minutes and cooled. The slurry is treated with 125 ml of conc. hydrochloric acid and filtered. The solid is washed with four 100 ml portions of water and the filtrate is evaporated in vacuo to a volume of 300 ml. This solution is cooled and mixed with a solution of 60 g of sodium hydroxide in 250 ml of cold water. The resulting solution is extracted with four 200 ml portions of ether and the ether solution is dried and evaporated in vacuo to give 30.7 g of oil. The oil is dissolved in 250 ml of ether, cooled to 0°C, and 33 g of ethyl chloroformate is added. A solution of 12 g of sodium hydroxide in 30 ml of water is added simultaneously with the second half of the ethyl chloroformate solution. After 1 hour at 10°C, the ether layer is washed with 5% hydrochloric acid, dried, and evaporated in vacuo to give 41.7 g of oil. Trituration with hexane and filtration gave 33 g of N-(2-phenyl-2-propenyl)ethyl carbamate, melting point 41°–42.5°C.

C. N-Nitroso-N-(2-phenyl-2-propenyl)ethyl carbamate

A solution of 21 ml (29.4 g) of nitrosyl chloride in 60 ml of pyridine (prepared at −25°C) is added over a period of 15 minutes to a solution of 57 g of N-(2-phenyl-2-propenyl)ethyl carbamate in 400 ml of pyridine at −5°C. The solution is stirred for 15 minutes and poured into 4 liters of cold water. The oil which separates is extracted into ether (three 600 ml portions) and the ether extract is washed successively with 1 liter of 10% hydrochloric acid, water, 1 liter of 5% sodium bicarbonate solution, and dried. Solvent removal gives 63 g of red oil that shows only minor impurities on TLC.

d. 2-Phenyl-3-diazo-1-propene

A solution of 63 g of N-nitroso-N-(2-phenyl-2-propenyl)ethyl carbamate in 300 ml of ether is added to 300 ml of 3M sodium methoxide in methanol at −1 to −2°C over a period of 30 minutes. The solution is stirred for a further hour and then poured into 2 liters of ice water and 100 ml each of ether and pentane. The organic layer is separated and kept at 0°C while the

EXAMPLE 6

9-Fluoro-2',3'-dihydro-11β,21-dihydroxypregn-4-eno-[16α,17-b][1,4]dioxin-3,20-dione A solution of 700 mg of 9-fluoro-2',3'-dihydro-11β,21-dihydroxypregn-4-eno[16α,17-b][1,4]dioxin-3,20-dione, 21-acetate (prepared as described in Example 5) in 75 ml of methanol is cooled to 0°C and 7 ml of 10% potassium carbonate solution is added. After 15 minutes, 20 ml of 20% aqueous acetic acid is added and the resulting solid is filtered and dried in vacuo to give 310 mg of 9-fluoro-2',3'-dihydro-11β,21-dihydroxypregn-4-eno[16α,17-b][1,4]-dioxin-3,20-dione, melting point 255°–258°C, dec.

EXAMPLE 7

21-Chloro-9-fluoro-2',3'-dihydro-11β,-hydroxy-5'-methylpregna-1,4-dieno[16α,17-b][1,4]dioxin-3,20-dione

A.

21-Chloro-9-fluoro-11β,16α,17-trihydroxypregna-1,4-diene-3,20-dione, 16,17-cycloborate A solution of 15.0 g of 21-chloro-9-fluoro-11β,16α,17-trihydroxypregna-1,4-diene-3,20-dione and 60 g of boric oxide in 750 ml of methanol is refluxed for 1 hour, cooled to 30°C and diluted with 1.5 liters of water. The resulting solid is filtered and dried in vacuo to give 13.85 g of 21-chloro-9-fluoro-11β,16α,17-trihydroxypregna-1,4-diene-3,20-dione, 16,17-cycloborate.

21-Chloro-9-fluoro-11β,17-dihydroxy-16α-[(2-methyl-2-propenyl)oxy]pregna-1,4-diene-3,20dione A solution of 2-methyl-3-diazo-1-propene in 150 ml of ether (prepared from 0.1 mole of N-(2-methyl-2-propenyl)-ethyl carbamate by the method of J. L. Brewbaker and H. Hart, *J. Am. Chem., Soc.*, 91, 711 (1969)) is diluted with 50 ml of methanol and cooled to 0°C. A total of 7 g of 21-chloro-9-fluoro-11β,16α,17-trihydroxypregna-1,4diene-3,20-dione, 16,17-cycloborate is added in portions until nitrogen evolution ceases. The solvent is removed in vacuo and the residue is dissolved in chloroform and chromatographed on an 80 g -silica gel column. Elution with chloroform gives TLC pure material which crystallizes from acetone-hexane to give 5.4 g of 21-chloro-9-fluoro-11β,17-dihydroxy-16α-[(2-methyl-2-propenyl)oxy]pregna-1,4-diene-3,20-dione, melting point 238°–240°C.

Anal. Calc'd for $C_{25}H_{32}ClFO_5$: C, 64.30; H, 6.91; Cl, 7.59; F, 4.06. Found: C, 64.53; H, 7.04; Cl, 7.74; F, 4.27.

C.

21-Chloro-9-fluoro-11β,17-dihydroxy-16α-[(2-methyl-oxiranyl)methoxy]pregna-1,4-diene-3,20-dione A solution of 3.0 g of 21-chloro-9-fluoro-11β,17-dihydroxy-16α-[(2-methyl-2-propenyl)oxy]pregna-1,4-diene-3,20-dione in 100 ml of dichloromethane is stirred with 1.4 g of m-chloroperbenzoic acid for 210 minutes. The solution is washed with a mixture of 10% potassium carbonate solution and 10% sodium sulfite solution, dried, and evaporated in vacuo to give an oil which solidifies on standing. Recrystallization from acetone-hexane gives 1.94 g as a first crop, and 820 mg as a second crop. Recrystallization of 600 mg of crop 1 from acetone-hexane gives 460 mg of 21-chloro-9-fluoro-11β,17-dihydroxy-16α-[(2-methyloxiranyl)methoxy]pregna-1,4-diene-3,20-dione, melting point 193°–236°C.

Anal. Calc'd for $C_{25}H_{32}ClFO_6$: C, 62.16; H, 6.68; Cl, 7.34; F, 3.93. Found: C, 62.19; H, 6.67; Cl, 7.52; F, 4.07.

(The nmr spectrum of this material indicates that it is ca. a 1:1 mixture of epimers at the quaternary oxirane carbon atom.)

D. 21-Chloro-9-fluoro-11β, 17-dihydroxy-16α-(2-oxopropoxy)pregna-1,4-diene-3,20-dione A solution of 2.16 g of 21-chloro-9-fluoro-11β,17-dihydroxy-16α-[(2-methyloxiranyl)methoxy]pregna-1,4-diene-3,20-dione in 50 ml of tetrahydrofuran is stirred with a solution of 5 g of periodic acid in 10 ml of water for 180 minutes. The solution is diluted with water and extracted with chloroform. The chloroform solution is dried and evaporated in vacuo and the residue is dissolved in chloroform and chromatographed on a 50 g-silica gel column. Elution with chloroform and collection of 50 ml fractions gives 1.81 g of TLC pure solid in fractions 9–17. Recrystallization from acetone-hexane gives 1.15 g of first crop material and 0.50 g in crops 2 and 3. Recrystallization from acetone-hexane of 600 mg of the first crop gives 490 mg of 21-chloro-9-fluoro-11β,17-dihydroxy-16α-(2-oxopropoxy)pregna-1,4-diene-3,20-dione, melting point 226°–227°C.

Anal. Calc'd for $C_{24}H_{30}ClFO_6$: C, 61.51; H, 6.45; Cl, 7.56; F, 4.05. Found: C, 61.69; H, 6.35; Cl, 7.53; F, 3.94.

21-Chloro-9-fluoro-2',3'-dihydro-11β-hydroxy-5'-methylpregna-1,4-dieno[16α,17-b][1,4]dioxin-3,20-dione A slurry of 100 mg of p-toluenesulfonic acid in 250 ml of benzene is refluxed with a Dean-Stark trap. The first 50 ml of benzene-water azeotrope is discarded and Linde type 4A molecular sieves are added to the trap. After 30 minutes at reflux, the solution is cooled and 980 mg of 21-chloro-9-fluoro-11β,17-dihydroxy-16α-(2-oxopropoxy)pregna-1,4-diene-3,20-dione is added. The resulting slurry is refluxed for 25 hours under nitrogen, cooled, and filtered to give 720 mg of solid. The filtrate is diluted with chloroform, washed with 5% sodium bicarbonate solution, water, dried, and evaporated to give 210 mg of material identical by TLC to the 720 mg of solid. These materials are combined, slurried with 50 ml of mineral oil, diluted with chloroform, and chromatographed on a 100 g — silica gel column. Elution with chloroform gives 850 mg of material which is recrystallized from acetone to give 487 mg of 21-chloro-9-fluoro-2',3'-dihydro-11β-hydroxy-5'-methylpregna-1,4-dieno[16α,17-b]-[1,4]dioxin-3,20-dione, melting point 259°–260°C.

Anal. Calc'd for $C_{24}H_{28}O_5FCl$: C, 63.92; H, 6.26; Cl, 7.86 F, 4.19. Found: C, 63.80; H, 6.49; Cl, 8.07; F, 4.13.

aqueous layer is extracted with 300 ml of ether. The combined organic layer is washed with two 1 liter portions of ice water, dried for 10 minutes at 0°C over NaOH pellets, and filtered to give 700 ml of red solution.

e. 9-Fluoro-11β,17,21-trihydroxy-16α-[(2-phenyl-2-propenyl)oxy]pregn-4-ene-3,20-dione The solution of 2-phenyl-3-diazo-1-propene prepared as described above is diluted with 150 ml of cold methanol and stirred well at 0°C as 13 g of 9-fluoro-11β,16α,17,21-tetrahydroxypregn-4-ene-3,20-dione, 16,17-cycloborate is added in portions. The slurry is stirred for 1 hour at 0°C and filtered to give 9.6 g of the title compound. The filtrate is stirred at room temperature for 1 hour with 4 g of the cycloborate and the resulting solution is cooled to 0°C and filtered to give 4.2 g of the title compound. The filtrate is evaporated in vacuo and the residue is dissolved in 400 ml of 3:1 ether-methanol and cooled to −10°C to give a further 3.0 g of material. A small sample recrystallized from acetone-hexane has a melting point of 161°–163.5°C.

B.
9-Fluoro-11β,17,21-trihydroxy-16α-[(2-phenyl-2-propenyl)oxy]pregn-4-ene-3,20-dione, 21-acetate A solution of 3.0 g of 9-fluoro-11β,17,21-trihydroxy-16α-[(2-phenyl-2-propenyl)oxy]pregn-4-ene-3,20-dione in 30 ml of pyridine is allowed to stand with 3 ml of acetic anhydride for 2 hours at room temperature. The solvent is removed in vacuo and the residue is dissolved in chloroform, washed with 5% hydrochloric acid, water, 5% sodium bicarbonate solution, and dried. Solvent removal gives an oil that crystallizes from acetone-hexane to give 2.3 g of material. Recrystallization of 600 mg from acetone-hexane gives 510 mg of 9-fluoro-11β,17,21-trihydroxy-16α-[(2-phenyl-2-propenyl)oxy]pregn-4-ene-3,20-dione, 21-acetate, melting point 169°–171°C.

Anal. Calc'd for $C_{32}H_{39}FO_7$: C, 69.29; H, 7.09; F, 3.42. Found: C, 69.13; H, 7.11; F, 3.26.

C.
9-Fluoro-11β,17,21-trihydroxy-16α-[(2-phenyl-oxiranyl)methoxy]pregn-4-ene3,20-dione, 21-acetate A solution of 555 mg of 9-fluoro-11β,17,21-trihydroxy-16α-[(2-phenyl-2-propenyl)oxy]pregn-4-ene-3,20-dione, 21-acetate in 25 ml of dichloromethane is stirred for 330 minutes with 200 mg of m-chloroperbenzoic acid. The solution is washed with 50 ml each of 5% sodium sulfite solution and 5% potassium carbonate solution. The dichloromethane solution is dried and evaporated to give 582 mg of product. Recrystallization from acetone-hexane gives 360 mg of 9-fluoro-11β,17,21-trihydroxy-16α-[(2-phenyl-oxiranyl)methoxy]pregn-4-ene-3,20-dione, 21-acetate.

D.
9-Fluoro-11β,17,21-trihydroxy-16α-(2-phenyl-2-oxoethoxy)pregn-4-ene-3,20-dione, 21-acetate A solution of 2.4 g of 9-fluoro-11β,17,21-trihydroxy-16α-[(2-phenyl-oxiranyl)methoxy]pregn-4-ene-3,20-dione, 21-acetate in 75 ml of tetrahydrofuran is stirred with a solution of 5 g of periodic acid in 20 ml of water for 270 minutes. The resulting slurry is diluted with 150 ml of water and the solid is filtered and dried in vacuo to give 1.79 g of crude product. This material is chromatographed on a 40 g-silica gel column. Elution with chloroform gives 1.6 g of TLC pure solid that is recrystallized from acetone-hexane to give 1.42 g of 9-fluoro-11β, 17,21-trihydroxy-16α-(2-phenyl-2-oxoethoxy)-pregn-4-ene-3,20-dione, 21-acetate, melting point 228°–230°C.

Anal. Calc'd for $C_{31}H_{37}FO_8$: C, 66.89; H, 6.70; F, 3.41. Found: C, 67.07; H, 6.69; F, 3.15.

E.
9-Fluoro-2',3'-dihydro-11β,21-dihydroxy-5'-phenyl-pregn-4-eno[16α,17-b][1,4]dioxin-3,20-dione, 21-acetate A slurry of 150 mg of p-toluenesulfonic acid in 300 ml of benzene is refluxed with a Dean-Stark trap. The first 50 ml of distillate is discarded, Linde 4A molecular sieves added, and the solution is refluxed for 30 minutes. The solution is cooled, 1.25 g of 9-fluoro-11β,17,21-trihydroxy-16α-(2-phenyl-2-oxoethoxy)-pregn-4-ene-3,20-dione, 21-acetate added, and the solution refluxed for 5 hours under nitrogen. The resulting solution is cooled, washed with 5% sodium bicarbonate solution, dried, and evaporated in vacuo. The residue is chromatographed on a 20 g-silica gel column. Elution with 1:1 hexane-chloroform gives 825 mg of crude product. This material is plate chromatographed on three 20 × 20 cm-2mm silica gel plates. After 2 developments with 1:1 chloroform-ethyl acetate the major UV-active band is excised and eluted with chloroform to give TLC pure material. Recrystallization from benzene gives 380 mg of 9-fluoro-2',3'-dihydro-11β,21-dihydroxy-5'-phenylpregn-4-eno-[16α,17-b][1,4]dioxin-3,20-dione, 21-acetate, melting point 145°–147°C.

Anal. Calc'd for $C_{31}H_{35}FO_7$: C, 69.13; H, 6.55; F, 3.53. Found: C, 68.90; H, 6.73; F, 3.58.

EXAMPLE 5

9-Fluoro-2',3'-dihydro-11β,21-dihydroxypregn-4-eno[16α,17-b][1,4]dioxin-3,20-dione, 21-acetate A slurry of 100 mg of p-toluenesulfonic acid in 250 ml of benzene is distilled to a volume of 200 ml and 1.0 g of 9-fluoro-5'ξ,11β,21-trihydroxypregn-4-eno[1-6α,17-b]-[1,4]dioxane-3,20-dione, 21-acetate (prepared as described in Example 1) is added. The resulting solution is refluxed with a Dean-Stark trap filled with 4A molecular sieves for 24 hours under nitrogen. The solution is cooled, diluted with chloroform, washed with 5% sodium bicarbonate solution, and dried. The residue obtained on solvent removal in vacuo is chromatographed on a 20 g — silica gel column. Elution with 1:1 dichloromethane-chloroform gives 510 mg of pure compound. Recrystallization from acetone-hexane gives 325 mg of TLC pure solid, in two crops. The mother liquor is purified by preparative thin layer chromatography on a 20 × 20 cm - 2 mm silica gel plate. After three developments with 9:1 chloroform-ethyl acetate, the major UV-active band is excised and eluted with chloroform-methanol. The residue obtained on solvent removal is crystallized from acetone-hexane to give 96 mg of pure material. This is combined with the 325 mg obtained above and recrystallized from acetone-hexane to give 312 mg of 9-fluoro-2',3'-dihydro-11β,21-dihydroxypregn-4-eno[16α,17-b]-[1,4]dioxin-3,20-dione, 21-acetate, melting point 231°–240°C, dec.

Anal. Calc'd for $C_{25}H_{31}FO_7$: C, 64.92; H, 6.76; F, 4.11. Found: C, 64.64; H, 6.54; F, 3.90.

EXAMPLE 8

5'ξ-Ethoxy-9-fluoro-11β,21-dihydroxypregn-4-eno[1-6α,17-b][1,4]dioxane-3,20-dione

A.
16α-(2,2Diethoxyethoxy)-9-fluoro-11β,17,21-trihydroxypregn-4-ene-3,20-dione A solution of 2,2-diethoxy-1-diazoethane (prepared from 0.0935 mole of N-2,2-diethoxyethyl urea by the method of W. Kirmse and M. Buschhoff, *Chem, Ber.* 100, 1491 (1967)) in 300 ml of 3:2 ether-pentane is diluted with 100 ml of methanol and cooled to 0°C. A total of 5.5 g of 9-fluoro-11β,16α,17,21-tetrahydroxypregn-4-ene-3,20-dione, 16,17-cycloborate is added in portions until nitrogen evolution ceases. The solvent is removed in vacuo and the residue is recrystallized from methanol to give 3.4 g of slightly impure material. This is dissolved in chloroform and chromatographed on an 80 g — silica gel column. Elution with chloroform gives 2.95 g of material which is recrystallized from acetone-hexane to give 2.6 g of 16α-(2,2-diethoxyethoxy)-9-fluoro-11β,17,21-trihydroxypregn-4-ene-3,20-dione, melting point 208°–210°C.

Anal. Calc'd for $C_{27}H_{41}FO_8$: C, 63.26; H, 8.07; F, 3.71. Found: C, 63.03; H, 7.86; F, 3.79.

B.
5'ξ-Ethoxy-9-fluoro-11β,21-dihydroxypregn-4-eno-[16α,17-b][1,4]dioxane-3,20-dione A slurry of 100 mg of p-toluenesulfonic acid in 250 ml of benzene is refluxed with a Dean-Stark trap. The first 50 ml of benzene-water azeotrope is discarded and Linde type 4A molecular sieves are added to the trap. After 30 minutes at reflux, the solution is cooled and 2 g of 16α-(2,2-diethoxyethoxy)-9-fluoro-11β,17,21-trihydroxypregn-4-ene-3,20-dione is added. The resulting slurry is refluxed for 2 hours under nitrogen, cooled, diluted with chloroform, washed with 5% sodium bicarbonate solution, water, dried and evaporated. The crude residue (2.25 g) is dissolved in chloroform and chromatographed on a 100 g — silica gel column. Elution with chloroform and 4:1 chloroform-ethyl acetate gives a total of 1.33 g of TLC pure material. Two recrystallizations from acetone-hexane (the last with charcoal) give 570 mg of 5'ξ-ethoxy-9-fluoro-11β,21-dihydroxypregn-4-eno[16α,17-b][1,4]-dioxane-3,20-dione, melting point 248°–250°C, dec.

Anal. Calc'd for $C_{25}H_{33}FO_7$: C, 64.64; H, 7.16; F, 4.10. Found: C, 64.75; H, 7.02; F, 3.95.

EXAMPLE 9

5'ξ-Methoxy-9-fluoro-11β,21-dihydroxypregn-4-eno[16α,17-b][1,4]dioxane-3,20-dione

A. 16α-(2,2-Dimethoxyethoxy)-9-fluoro-11β,17,21-trihydroxypregn-4-ene-3,20-dione A solution of 2,2-dimethoxy-1-diazoethane in 100 ml of 6:4 pentane-ether (prepared by the method of W. Kirmse and M. Buschhoff, *Chem. Ber.*, 100, 1491 (1967) utilized for the diethoxy analog) is diluted with 50 ml of methanol and cooled to 0°C. A total of 2 g of 9-fluoro-11β,16α,17,21-tetrahydroxypregn-4-ene-3,20-dione, 16,17-cycloborate is added. After nitrogen evolution ceases the solvent is removed in vacuo and the residue is dissolved in chloroform and chromatographed on an alumina column (neutral, activity III). Elution with chloroform gives 485 mg of slightly impure material and then 1.27 g of TLC pure compound. Recrystallization of the 485 mg from acetone-hexane gives 175 mg of TLC homogeneous solid which is combined with the 1.27 g and recrystallized from acetone-hexane to give 1.09 g of 16α-(2,2-dimethoxyethoxy)-9-fluoro-11β,17,21-trihydroxypregn-4-ene-3,20-dione, melting point 192°–194°C.

Anal. Calc'd for $C_{25}H_{37}FO_8$: C, 61.96; H, 7.70; F, 3.94. Found: C, 62.21; H, 7.79; F, 3.85.

B.
5'ξ-Methoxy-9-fluoro-11β,21-dihydroxypregn-4-eno[16α,17-b][1,4]dioxane-3,20-dione Following the procedure of Example 8B, but substituting 16α-(2,2-dimethoxyethoxy)-9-fluoro-11β,17,21-trihydroxypregn-4-ene-3,20-dione for the 2,2-diethoxyethoxy steroid, the title compound is obtained.

EXAMPLE 10

21-Chloro-5'ξ-ethoxy-9-fluoro-11β-hydroxypregn-4-eno[16α,17-b][1,4]dioxane-3,20-dione

A.
5'ξ-Ethoxy-9-fluoro-11β,21-dihydroxypregn-4-eno[1-6α,17][1,4]dioxane-3,20-dione, 21-mesylate A solution of 950 mg of 5'ξ-ethoxy-9-fluoro-11β,21-dihydroxypregn-4-eno[16α,17-b][1,4]dioxane-3,20-dione (prepared as described in Example 8) in 10 ml of pyridine is stirred at 0°C with 3 ml of methanesulfonyl chloride for 150 minutes. Ice is added and the mixture poured into cold, dilute hydrochloric acid and extracted with chloroform. The chloroform solution is dried and evaporated in vacuo to give 1.0 of crude mesylate.

B.
21-Chloro-5'ξ-ethoxy-9-fluoro-11β-hydroxypregn-4-eno[16α,17-b][1,4]dioxane-3,20-dione A solution of 1 g of 5'ξ-ethoxy-9-fluoro-11β,21-dihydroxypreg-4-eno[16α,17-b][1,4]dioxane-3,20-dione, 21-mesylate in 100 ml of dimethylformamide is refluxed with 4 g of lithium chloride for 30 minutes, cooled, and poured into ice-water. The resulting solid is filtered, washed well with water, and dried in vacuo to give 782 mg of product. This material is dissolved in chloroform and chromatographed on a 20 g — silica gel column. Elution with chloroform gives 715 mg of TLC pure solid. Recrystallization from acetone-lexane gives 600 mg of 21-chloro-5'ξ-ethoxy-9-fluoro-11β-hydroxypregn-4-eno[16α,-17-b][1,4]dioxane-3,20-dione, melting point 235°–237°C, dec.

Anal. Calc'd for $C_{25}H_{34}ClFO_6$: C, 61.91; H, 7.07; Cl, 7.31: F, 3.92. Found: C, 61.75; H, 7.27; Cl, 7.24; F, 3.85.

EXAMPLE 11

9-Fluoro-5'ξ,11β,21-trihydroxypregn-4-eno[16α,17-b]-[1,4]dioxane-3,20-dione

A solution of 1.6 g of 16α-(2,2-diethoxyethoxy)-9-fluoro-11β,17,21-trihydroxypregn-4-ene-3,20-dione (prepared as described in Example 8A) in 200 ml of tetrahydrofuran is refluxed with 20 ml of 1N hydrochloric acid for 3 hours. The solution is cooled, evaporated in vacuo to one third the original volume, and diluted with water. The resulting solid is filtered and dried in vacuo to give 800 mg of product. Recrystallization from methanol give 350 mg of 9-fluoro-5′ξ,11β,21-trihydroxypregn-4-eno-[16α,17-b][1,4]dioxane-3,20-dione, melting point 260°–262°C, dec.

Anal. Calc'd for $C_{23}H_{31}FO_7$: C, 63.00; H, 7.13; F, 4.33. Found: C, 62.96; H, 7.07; F, 4.48.

EXAMPLE 12

9-Fluoro-5′ξ,11β,21-trihydroxypregn-4-eno[16α,17-b]-[1,4]dioxane-3,20-dione, 5′,21-diacetate To a solution of 1.3 g of 9-fluoro-5′ξ,11β11β,21-trihydroxypregn-4-eno[16α,17-b][1,4]dioxane-3,20-dione (prepared as described in Example 11) in 10 ml of pyridine is added 5 ml of acetic anhydride. The solution is kept at room temperature for 4 hours. The solvent is removed in vacuo and the residue dissolved in chloroform, washed with dilute hydrochloric acid, and dried. The solvent is removed in vacuo and the residue dissolved in chloroform and chromatographed onn a silica gel column. Elution with chloroform gives 730 mg of impure compound and 506 mg of TLC pure material. The 730 mg of impure material is dissolved in chloroform and plate-chromatographed on two 20 × 20 cm — 2 mm silica gel plates. After three developments with 1:1 chloroform-ethyl acetate, the UV-active band of lowest $R_f$ is excised and eluted with chloroform. The chloroform is removed in vacuo and the residue combined with the 506 mg of pure material and recrystallized from acetone-hexane to give 530 mg of 9-fluoro-5′ξ,11β,21-trihydroxypregn-4-eno[16α,17-b][1,4]dioxane-3,20-dione, 5′,21-diacetate, melting point 195°–197°C.

Anal. Calc'd for $C_{25}H_{35}FO_9$: C, 62.42; H, 6.21; F, 3.66. Found: C, 62.37; H, 6.44; F, 3.61.

EXAMPLE 13

9-Fluoro-5′ξ,11β,21-trihydroxypregn-4-eno[16α,17-b]-[1,4]dioxane-3,20-dione, 5′-valerate, 21acetate A solution of 9-fluoro-5′ξ,11β,21-trihydroxypregn-4-eno[16α,17-b][1,4]dioxane-3,20-dione, 21-acetate (prepared as described in Example 1) in pyridine is stirred with excess valeric anhydride for 2 hours. The solvent is removed in vacuo and the residue dissolved in chloroform. The chloroform solution is washed with 5% hydrochloric acid, water, 5% sodium bicarbonate, and dried. Solvent removal yields 9-fluoro-5′ξ,11β,21-trihydroxypregn-4-eno[16α,17-b][1,4]dioxane-3,20-dione, 5′-valerate, 21-acetate.

EXAMPLE 14

21-Chloro-9-fluoro-5′ξ,11β-dihydroxypregna-1,4-dieno[16α,17-b][1,4]dioxane-3,20-dione

A.

21-Chloro-16α-(2,2-diethoxyethoxy)-9-fluoro-11β,17-dihydroxypregna-1,4-diene-3,20-dione A solution of 2,2-diethoxy-1-diazoethane (prepared from 0.0935 mole of N-2,2-diethoxyethyl urea by the method of W. Kirmse and M. Buschhoff, Chem. Ber., 100, 1491 (1967)) in 300 ml of 3:2 ether-pentane is diluted with 100 ml of methanol and cooled to 0°C. A total of 2.5 g of 21-chloro-9-fluoro-11β,16α,17-trihydroxypregna-1,4-diene-3,20-dione, 16,17-cycloborate is added in portions until nitrogen evolution ceases. The solvent is removed in vacuo and the residue is dissolved in chloroform and chromatographed on an 80 g — silica gel column. Elution with chloroform gives 2.16 g of TLC pure material that is recrystallized from acetone-hexane to give 1.75 g of 21-chloro-16α-(2,2-diethoxyethoxy)-9-fluoro-11β,17-dihydroxypregna-1,4-diene-3,20-dione, melting point 200°–202°C.

Anal. Calc'd for $C_{27}H_{38}ClFO_7$: C, 61.30; H, 7.24; Cl, 6.70: F, 3.59. Found: C, 61.55; H, 7.24; Cl, 6.68; F, 3.47.

B.

21-Chloro-9-fluoro-5′ξ,11β-dihydroxypregna-1,4-dieno[16α,17-b][1,4]dioxane-3,20-dione A solution of 1.6 g of 21-chloro-16α-(2,2-diethoxyethoxy)-9-fluoro-11β,17-dihydroxypregna-1,4-diene-3,20-dione in 200 ml of tetrahydrofuran is refluxed with 20 ml of 1N hydrochloric acid for 5 ½ hours. The solvent is removed in vacuo and the residue is diluted with water, extracted with chloroform, and the chloroform solution is washed with 5% sodium bicarbonate solution, water, dried, and evaporated. The residue is dissolved in chloroform and chromatographed on a 60 g — silica gel column. Elution with a mixture of 3:2 chloroform:ethyl acetate gives 1.29 g of pure material which is recrystallized from acetonitrile to give 940 mg of 21-chloro-9-fluoro-5′ξ,11β-dihydroxypregna-1,4-dieno[16α,17-b][1,4]dioxane-3,20-dione, melting point 242°–245°C, dec. Anal. Calc'd for $C_{23}H_{28}O_6ClF$; C, 60.72; H, 6.20; Cl, 7.79; F, 4.18. Found: C, 60.52; H, 5.97; Cl, 7.86; F, 4.03.

EXAMPLE 15

21-Chloro-9-fluoro-5′ξ,11β-dihydroxypregna-1,4-dieno[16α,17-b][1,4]dioxane-3,20-dione, 5′-acetate To a solution of 887 mg of 21-chloro-9-fluoro-5′ξ,11β-dihydroxypregna-1,4-dieno[16α,17-b][1,4]dioxane-3,20-dione (prepared as described in Example 14) in 5 ml of pyridine is added 2 ml of acetic anhydride. The solution is kept at ambient temperature for 4 hours. The solvent is removed in vacuo and the residue is dissolved in chloroform, washed with dilute hydrochloric acid, and dried. The solvent is removed in vacuo and the residue is dissolved in chloroform and chromatographed on a silica gel column. Elution with chloroform gives 748 mg of material. Recrystallization from acetone-hexane gives 505 mg of slightly impure material. A second recrystallization from methanol gives 420 mg of TLC pure 21-chloro-9-fluoro-5′ξ,11β-dihydroxypregna-1,4-dieno[16α,17-b][1,4]-dioxane-3,20-dione, 5′-acetate, melting point 242°–244°C, dec.

Anal. Calc'd for $C_{25}H_{30}O_7FCl$: C, 58.41; H, 6.39; Cl, 7.50; F, 4.02. Found: C, 58.23; H, 6.23; Cl, 7.40; F, 4.08.

EXAMPLE 16

21-Chloro-9-fluoro-2′,3′-dihydro-11β-hydroxypregna-1,4-dieno[16α,17-b][1,4]dioxin-3,20-dione A slurry of 300 mg of p-toluenesulfonic acid in 1.1 liters of benzene is refluxed with a Dean-Stark trap. The first 100 ml of distillate is discarded, Linde 4A molecular sieves are added to the trap and the solution is refluxed for 30 minutes. The solution is cooled, 2.0 g of 21-chloro-9-fluoro-5′ξ,11β-dihydroxypregna-1,4-dieno[16α,17-b][1,4]-dioxane-3,20-dione (prepared as described in Example 14) is added, and the resulting slurry is refluxed for 36 hours under nitrogen. The slurry is cooled and the benzene is removed in vacuo. The residue is dissolved in chloroform and the chloroform solution washed with 5% sodium bicarbonate solution, water, dried, and evaporated in vacuo. The residue is dissolved in chloroform and chromatographed on a 50 g — silica gel column. Elution with chloroform gives 985 mg of solid which is recrystallized from acetone-hexane to give 528 mg of 21-chloro-9-fluoro-2′,3′-dihydro-11β-hydroxypregna-1,4-dieno[16α,17-b][1,4]dioxin-3,20-dione, melting point 248°–250°C, dec.

Anal. Calc'd for $C_{23}H_{26}ClFO_5$: C, 63.23; H, 6.00; Cl, 8.12; F, 4.35. Found: C, 62.95; H, 5.88; Cl, 8.24; F, 4.22.

EXAMPLE 17

9-fluoro-11β,21-dihydroxypregn-4-eno[16α,17-b][1,4]-dioxane-3,5′,20-trione, 21-acetate A solution of 1.2 g of 9-fluoro-5′ξ,11β,21-trihydroxypregn-4-eno[16α,17-b][1,4]dioxane-3,20-dione, 21-acetate (prepared as described in Example 1) in 250 ml of toluene is slurried with 22 g of Fetizon's reagent (V. Balogh, M. Fetizon and M. Golfier, *Angew. Chem. Internat. Edit.*, 8, 444 (1969)) and distilled to a volume of 200 ml. The resulting slurry is refluxed under nitrogen for 12 ½ hours, cooled, filtered, and the resulting solid is washed well with chloroform. The filtrate and washings are combined, evaporated in vacuo, and the residue chromatographed on a 40 g — silica gel column. Elution with chloroform gives 270 mg of oil which crystallizes from acetone-hexane to give 181 mg of TLC pure solid. This is combined with 151 mg of identical material, obtained from repeating this reaction on a 1 g scale, and recrystallized from acetone-hexane to give 275 mg of 9-fluoro-11β,21-dihydroxypregn- 4-eno[16α,17-b][1,4]dioxane-3,5′, 20-trione, 21-acetate, melting point 217.5°–220°C, dec.

Anal. Calc'd for $C_{25}H_{31}FO_8$: C, 62.75; H, 6.53; F, 3.97. Found: C, 62.61; H, 6.53; F, 3.73.

EXAMPLE 18

9-Fluoro-11β,21-dihydroxypregn-4-eno[16α,17-b]-[1,4]dioxane-3,20-dione, 21-acetate

A. 9-Fluoro-11β,17,21-trihydroxy-16α-[2-(tetrahydropyran-2-yloxy)ethoxy]pregn-4-ene-3,20-dione a. Tetrahydropyran-2-yloxy acetonitrile This material is prepared by the method of J. Davoll and D. H. Laney, *J. Chem. Soc.* 2129 (1956) and has a boiling point of 78°–79°C at 2 mm.

b. 2-(Tetrahydropyran-2-yloxy)ethylamine

A solution of 35 g of tetrahydropyran-2-yloxy acetonitrile in 100 ml of ether is added dropwise to a slurry of 10 g of lithium aluminum hydride in 300 ml of ether and 100 ml of tetrahydrofuran. The slurry is refluxed for 210 minutes, cooled, and 25 ml of sat. potassium carbonate solution is added at a rate that maintains gentle reflux. After 90 minutes the slurry is filtered and the solid is washed with ether. The filtrate is evaporated in vacuo and distilled to give 33.6 g of 2-(tetrahydropyran-2-yloxy)ethylamine, boiling point 41.5°–46°C at 0.5–0.8 mm.

c. N-[2-(Tetrahydropyran-2-yloxy)ethyl]urea

A mixture of 33.2 g of 2-(tetrahydropyran-2-yloxy) ethylamine, 50 g of ice, and a solution of 35 g of potassium isocyanate in 80 ml of water is stirred well as 45.6 ml of 5N hydrochloric acid (cooled to −40°C) is added in one portion. The resulting solution is refluxed for 90 minutes, cooled, and extracted with four 150 ml portions of chloroform. The chloroform extract is dried and evaporated in vacuo to give 39.6 g of oil.

d. N-nitroso-N-[2-(tetrahydropyran-2-yloxy) ethyl]urea

A solution of 39.6 g of N-2-(tetrahydropyran-2-yloxy)urea in 400 ml of ether and 100 ml of methylene chloride is slurried with 50 g of sodium acetate and cooled to −10°C with mechanical stirring. A solution of 30 g of nitrogen dioxide in 100 ml of ether is added over a 30 minute period, the slurry is stirred at −10°C for 20 minutes and then filtered. The filtrate is washed with saturated sodium bicarbonate solution, dried, and evaporated to give 41.8 g of yellow oil.

e. 2-(Tetrahydropyran-2-yloxy)-1-diazoethane

A solution of 41.8 g of N-nitroso-N-[2-(tetrahydropyran-2-yloxy)ethyl]urea in 200 ml of ether and 100 ml of pentane is added to 450 ml of 1N sodium hydroxide solution at 1°–4°C over a 25 minute period. The solution is stirred for an additional 30 minutes and the layers are separated. The organic layer is dried over sodium hydroxide pellets at 0°C for 5 minutes, and then filtered.

f. 9-Fluoro-11β,17,21-trihydroxy-16α-[2-tetrahydropyran-2-yloxy)ethoxy]pregn-4-ene-3,20-dione A solution of 2-(tetrahydropyran-2-yloxy)-1-diazoethane (prepared from 0.21 mole of precursor) in 400 ml of 3:1 ether-pentane is diluted with 100 ml of cold methanol and stirred well as 5.0 g of 9-fluoro-11β,16α,17,21-tetrahydroxypregn-4-ene-3,20-dione, 16,17-cycloborate is added in portions. When nitrogen evolution ceases, the slurry is filtered to give 0.4 g of recovered borate. The filtrate is evaporated in vacuo to give an oil that is dissolved in chloroform and chromatographed on a 150 g — silica gel column. Elution with 1:1 chloroform-ethyl acetate gives 4.0 g of TLC pure product. A small sample of similar material is recrystallized from acetone-hexane to give 9-fluoro-11β,17,21-trihydroxy-16α-[2-(tetrahydropyran-2-yloxy)ethoxy]pregn-4-ene-3,20-dione, melting point 196°–200°C.

B. 9-Fluoro-11β,17,21-trihydroxy-16α-[2-(tetrahydropyran-2-yloxy)ethoxy]pregn-4-ene-3,20-dione, 21-acetate A solution of 4.0 g of 9-fluoro-11β,17,21-trihydroxy-16α-[2-(tetrahydropyran-2-yloxy)ethoxy]pregn-4-ene-3,20-dione in 50 ml of pyridine is allowed to stand with 5 ml of acetic anhydride for 3 hours. The solvents are removed in vacuo and the residue is dissolved in chloroform and washed with 5% hydrochloric acid, water, and 5% sodium bicarbonate solution. Drying and solvent removal gives 4.4 g of crude product. Crystallization of a similar sample from acetone-hexane gives 9-fluoro-11β,17,-21-trihydroxy-16α-[2-( 2-yloxy)ethoxy]-pregn-4-ene-3,20-dione, 21-acetate, melting point 150°–152°C.

C. 9-Fluoro-11β,17,21-trihydroxy-16α-(2-hydroxyethoxy)-pregn-4-ene-3,20-dione, 21-acetate

Method A

A solution of 4.4 g of 9-fluoro-11β,17,21-trihydroxy-16α-[2-(tetrahydropyran-2-yloxy)ethoxy]pregn-4-ene-3,20-dione, 21-acetate in 60 ml each of acetic acid and water is stirred for 4 hours and the bulk of the solvent removed in vacuo. The residue is dissolved in chloroform and washed with 5% sodium bicarbonate solution. Drying and solvent removal gives an oil which crystallizes from acetone-hexane to give 2.4 g of 9-fluoro-11β,17,21-trihydroxy-16α-(2-hydroxyethoxy)pregn-4-ene-3,20-dione, 21-acetate, melting point 162°–165°C.

Method B

A solution of 1.98 g of 9-fluoro-5′ξ,11β,21-trihydroxypregn-4-eno-[16α,17-b][1,4]dioxane-3,20-dione, 21-acetate (prepared as described in Example 1) in 100 ml of methanol is cooled to 0°C and 148 mg of sodium borohydride is added. After 9 minutes the solution is poured into a mixture of ice and 5% hydrochloric acid and extracted with chloroform to give 1.78 g of oil. This material is chromatographed on a 50 g — silica gel column. Elution with 19:1 chloroform-ethyl acetate gives 0.45 g of pure 9-fluoro-11β,17,21-trihydroxy-16α-(2-hydroxyethoxy)-pregn-4-ene-3,20-dione, 21-acetate and a total of 0.35 g of impure material.

D.
9-Fluoro-16α-(2-mesyloxyethoxy)-11β,17,21-trihydroxypregn-4-ene-3,20-dione, 21-acetate A solution of 0.80 g of 9-fluoro-16α-(2-hydroxyethoxy)-11β,17,21-trihydroxypregn-4-ene-3,20-dione, 21-acetate in 10 ml of pyridine is stirred with 0.5 ml of methanesulfonyl chloride for 90 minutes at 0°C under nitrogen. The solution is poured into cold 5% hydrochloric acid and extracted with chloroform. The chloroform extract is dried and evaporated to give an oil which is chromatographed on a 20 g — silica gel column. Elution with chloroform gives 521 mg of TLC pure 9-fluoro-16α-(2-mesyloxyethoxy)-11β,17,21-trihydroxypregn-4-ene-3,20-dione, 21-acetate.

E.
9-Fluoro-11β,21-dihydroxypregn-4-eno[16α,17-b][1,4]-dioxane-3,20-dione, 21-acetate A solution of 521 mg of 9-fluoro-16α-(2-mesyloxyethoxy)-11β,17,21-trihydroxypregn-4-ene-3,20-dione, 21-acetate in 40 ml of dimethylsulfoxide is stirred at 110°C under nitrogen for 2 hours with 600 mg of sodium bicarbonate (dried at 110°C in vacuo). The solution is cooled, poured into 5% hydrochloric acid and extracted with chloroform. The chloroform extract is washed twice with 2% hydrochloric acid, dried, and evaporated in vacuo to give 421 mg of oil. This material is chromatographed on a 20 g — silica gel column. Elution with chloroform gives 331 mg of TLC pure material which solidifies. Recrystallization from acetone-hexane gives 215 mg of 9-fluoro-11β,21-dihydroxypregn-4-eno[16α,17-b][1,4]dioxane-3,20-dione, 21-acetate, melting point 275°–280°C, dec.

Anal. Calc'd for $C_{25}H_{33}FO_7$: C, 64.64; H, 7.16; F, 4.09. Found: C, 64.59; H, 7.21; F, 3.98.

EXAMPLE 19

21-Chloro-9-fluoro-5′ξ,11β-dihydroxypregn-4-eno-[16α,17-b][1,4]dioxane-3,20-dione

A.
16α-Allyloxy-9-fluoro-11β,17,21-trihydroxypregn-4-ene-3,20-dione, 21-methanesulfonate A solution of 1.0 g of 16α-allyloxy-9-fluoro-11β,17,21-trihydroxypregn-4-ene-3,20-dione (prepared as described in Example 1A) in 15 ml of pyridine is stirred at 0°C under nitrogen for 150 minutes with 0.35 ml of methanesulfonyl chloride. The resulting solution is poured into cooled 5% hydrochloric acid and extracted with chloroform. The chloroform solution is washed with water, dried, and evaporated in vacuo to give 1.05 g of residue.

B.
16α-Allyloxy-21-chloro-9-fluoro-11β,17-dihydroxypregn-4-ene-3,20-dione

A solution of 1.05 of 16α-allyloxy-9-fluoro-11β,17,21-trihydroxypregn-4-ene-3,20-dione, 21-methanesulfonate in 65 ml of dimethylformamide is refluxed for 1 hour under nitrogen with 1.05 g of lithium chloride. The solution is cooled, diluted with 400 ml of water and filtered. The solid is dissolved in chloroform, washed with 5% hydrochloric acid, water, dried, and evaporated in vacuo to give 800 mg of residue. This material is dissolved in chloroform and chromatographed on an 18 g — silica gel column. Elution with chloroform gives 600 mg of TLC pure material. Two recrystallizations from acetone-hexane give 500 mg of 16α-allyloxy-21-chloro-9-fluoro-11β,17-dihydroxypregn-4-ene-3,20-dione, melting point 224°–225°C.

Anal. Calc'd for $C_{24}H_{32}ClFO_5$: C, 63.36; H, 7.09; Cl, 7.79; F, 4.18. Found: C, 63.53; H, 6.97; Cl, 7.50; F, 4.14.

C.
21-Chloro-9-fluoro-11β,17-dihydroxy-16α-(oxiranylmethoxy)pregn-4-ene-3,20-dione Following the procedure of Example 1C, but substituting 16α-allyloxy-21-chloro-9-fluoro-11β,17-dihydroxypregn-4-ene-3,20-dione for 9-fluoro-16α-allyloxy-11β,17,21-trihydroxypregn-4-ene-3,20-dione, 21-acetate, the title compound is obtained.

D.
21-Chloro-9-fluoro-5′ξ,11β-dihydroxypregn-4-eno-[16α,17-b][1,4]dioxane-3,20-dione Following the procedure of Example 1D, but substituting 21-chloro-9-fluoro-11β,17-dihydroxy-16α-(oxiranylmethoxy)pregn-4-ene-3,20-dione for 9-fluoro-11β,17,21-trihydroxy-16α-(oxiranyl-methoxy)pregn-4-ene-3,20-dione, 21-acetate, the title compound is obtained.

EXAMPLE 20

21-Chloro-9-fluoro-2′,3′-dihydro-11β-hydroxy-5′-phenylpregna-1,4-dieno[16α,17-b][1,4]dioxin-3,20-dione

A.
21-Chloro-9-fluoro-11β,17-dihydroxy-16α-[(2-phenyl-2-propenyl)oxy]pregna-1,4-diene-3,20-dione A solution of 2-phenyl-3-diazo-1-propene (prepared from 28.5 g of N-(2-phenyl-2-propenyl)ethyl carbamate, prepared as described in Example 4) in 700 ml of ether and 50 ml of pentane is diluted with 150 ml of methanol at 0°C and 10 g of 21-chloro-9-fluoro-11β,16α,17-trihydroxypregna-1,4-diene-3,20-dione, 16,17-cycloborate is added in portions. After nitrogen evolution ceases the solvents are removed in vacuo and the residue is recrystallized from methanol to give 6.1 g of 21-chloro-9-fluoro-11β,17-dihydroxy-16α-[(2-phenyl-2-propenyl)oxy]-pregna-1,4-diene-3,20-dione, melting point 212°–214°C.

Anal. Calc'd. for $C_{30}H_{34}ClFO_5$: C, 68.11; H, 6.48; Cl, 6.70; F, 3.59. Found: C, 68.37; H, 6.75; Cl, 6.92; F, 3.49.

B. 21-Chloro-9-fluoro-11β,17-dihydroxy-16α-[(2-phenyloxiranyl)methoxy]pregna-1,4-diene-3,20-dione A solution of 4.0 g of 21-chloro-9-fluoro-11β,17-dihydroxy-16α-[(2-phenyl-2-propenyl)oxy]pregna-1,4-diene-3,20-dione in 100 ml of dichloromethane is stirred with 1.6 g of m-chloroperbenzoic acid for 1 hour at room temperature. The resulting solution is washed with a mixture of 100 ml each of 5% sodium sulfite solution and 5% sodium bicarbonate solution, dried, and evaporated in vacuo to give 4.8 g of crude 21-chloro-9-fluoro-11β,17-dihydroxy-16α-[(2-phenyloxiranyl)methoxy]pregna-1,4-diene-3,20-dione.

C. 21-Chloro-9-fluoro-11β,17-dihydroxy-16α-(2-oxo-2-phenylethoxy)pregna-1,4-diene-3,20-dione A solution of 4.8 g of 21-chloro-9-fluoro-11β,17-dihydroxy-16α-[(2-phenyloxiranyl)methoxy]pregna-1,4-diene-3,20-dione in 150 ml of tetrahydrofuran is stirred with a solution of 10 g of periodic acid in 40 ml of water for 4 hours. The resulting slurry is diluted with 1 liter of water and filtered. The solid is dried in vacuo and recrystallized from methanol-chloroform to give 2.4 g of 21-chloro-9-fluoro-11β,17-dihydroxy-16α-(2-oxo-2-phenylethoxy)pregna-1,4-diene-3,20-dione, melting point 266°–268°C, dec.

Anal. Calc'd. for $C_{29}H_{32}ClFO_6$: C, 65.59; H, 6.08; Cl, 6.68; F, 3.58. Found: C, 65.28; H, 6.38; Cl, 6.62; F, 3.47.

D. 21-Chloro-9-fluoro-2',3'-dihydro-11β-hydroxy-5'-phenylpregna-1,4-dieno[16α,17-b][1,4]-dioxin-3,20-dione A slurry of 150 mg of p-toluenesulfonic acid in 750 ml of benzene is refluxed with a Dean-Stark trap. The first 150 ml of benzene-water azeotrope is discarded and Linde type 4A molecular sieves are added to the trap. After 30 minutes at reflux, the solution is cooled and 1.0 g of 21-chloro-9-fluoro-11β,17-dihydroxy-16α-(2-oxo-2-phenylethoxy)pregna-1,4-diene-3,20-dione is added. The resulting slurry is refluxed for 6 hours under nitrogen, cooled, washed with 5% sodium bicarbonate solution, water, dried and evaporated in vacuo to give 955 mg of crude product. This material is dissolved in chloroform and chromatographed on a 40-g silica gel column. Elution with chloroform gives TLC pure material which fails to crystallize and is rechromatographed on a 20-g silica gel column. Elution with 3:1 chloroform-hexane gives 525 mg of solid. Recrystallization from ethyl acetate-hexane gives 443 mg of 21-chloro-9-fluoro-2',3'-dihydro-11β-hydroxy-5'-phenylpregna-1,4-dieno[16α,17-b][1,4]dioxin-3,20-dione, melting point 195°–197°C.

Anal. Calcd. for $C_{29}H_{30}ClFO_5$: C, 67.89; H, 5.90; Cl, 6.91; F, 3.71. Found: C, 68.02; H, 5.84; Cl, 6.70; F, 3.59.

EXAMPLE 21

21-Chloro-9-fluoro-11β-hydroxypregna-1,4-dieno[16α,17-b][1,4]dioxane-3,20-dione

A. 21-Chloro-9-fluoro-11β,17-dihydroxy-16α-[2-(tetrahydropyran-2-yloxy)ethoxy]pregna-1,4-diene-3,20-dione A solution of 2-tetrahydropyran-2-yloxy)-1-diazoethane (prepared from 0.21 mole of N-[2-tetrahydropyran-2-yloxy)ethyl]urea as described in Example 18) in 400 ml of 3:1 ether-pentane is diluted with 100 ml each of ether and methanol at 0°C and stirred vigorously while 5.0 g of 21-chloro-9-fluoro-11β,16α,17-trihydroxypregna-1,4-diene-3,20-dione, 16,17-cycloborate is added. After nitrogen evolution ceases the solvents are removed in vacuo and the residue dissolved in chloroform and chromatographed on a 100 g-silica gel column. Elution with chloroform give 3.6 g of solid. Recrystallization from acetone-hexane gives 3.26 g of 21-chloro-9-fluoro-11β,17-dihydroxy-16α-[2-(tetrahydropyran-2-yloxy)ethoxy]pregna-1,4-diene-3,20-dione, melting point 168°–170°C.

B. 21-Chloro-9-fluoro-11β,17-dihyroxy-16α-(2-hydroxyethoxy)pregna-1,4-diene-3,20-dione A solution of 4.2 g of 21-chloro-9-fluoro-11β,17-dihydroxy-16α-[2-tetrahydropyran-2-yloxy)ethoxy]pregna-1,4-diene-3,20-dione in 150 ml of acetic acid and 75 ml of water is stirred at room temperature for 6 hours, diluted with 1.5 liter of cold water, and the resulting solid filtered and dried in vacuo to give 2.63 g. Recrystallization from acetone-hexane gives 2.03 g of 21-chloro-9-fluoro-11β,17-dihydroxy-16α-(2-hydroxyethoxy)pregna-1,4-diene-3,20-dione, melting point 226°–228°C, dec.

Anal. Calcd. for $C_{23}H_{30}ClFO_6$: C, 60.46; H, 6.62; Cl, 7.76; F, 4.16. Found: C, 60.26; H, 6.49; Cl, 7.88; F, 4.26.

C. 21-Chloro-9-fluoro-11β,17-dihydroxy-16α-(2-mesyloxyethoxy)pregna-1,4-diene-3,20-dione A solution of 1.5 g of 21-chloro-9-fluoro-11β,17-dihydroxy-16α-(2-hydroxyethoxy)pregna-1,4-diene-3,20-dione in 25 ml of pyridine is cooled to 0°C and 0.6 ml of methanesulfonyl chloride is added. After 2 hours the mixture is poured into cold dilute hydrochloric acid and extracted with chloroform. The chloroform solution is dried and evaporated in vacuo to 2.0 g of crude mesylate.

D. 21-Chloro-9-fluoro-11β-hydroxypregna-1,4-dieno[16α,17-b][1,4]dioxane-3,20-dione A solution of 2.0 g of 21-chloro-9-fluoro-11β,17-dihydroxy-16α-(2-mesyloxyethoxy)pregna-1,4-diene-3,20-dione in 100 ml of dimethylsulfoxide is stirred at 110°C under nitrogen with 2.0 g of sodium bicarbonate (dried at 110°C in vacuo). After 1 hour the slurry is cooled, poured into 2 liters of 2.5% hydrochloric acid, and extracted with chloroform. The chloroform solution is washed twice with dilute hydrochloric acid, dried, and evaporated in vacuo to give 1.4 g of crude product. This material is dissolved in chloroform and chromatographed on a 100 g-silica gel column. Elution with chloroform gives 880 mg of material which crystallizes from methanol-chloroform to give 405 mg of 21-chloro-9-fluoro-11β-hydroxypregna-1,4-dieno[16α,17-b][1,4]dioxane-3,20-dione, melting point 320°–321°C, dec.

Anal. Calcd for $C_{23}H_{28}ClFO_5$: C, 62.94; H, 6.43; Cl, 8.08; F, 4.33. Found: C, 62.73; H, 6.20; Cl, 8.27; F, 4.27.

EXAMPLE 22

11β,21-Dihydroxypregna-1,4-dieno[16α,17-b][1,4]-dioxane-3,20-dione, 21-acetate

A.

16α-[2-(Tetrahydropyran-2-yloxy)ethoxy]-11β,17,21-trihydroxypregna-1,4-diene-3,20-dione A solution of 2-(tetrahydropyran-2-yl)oxy-1-diazoethane (prepared from 69.1 g of N-[2-(tetrahydropyran-2-yl-oxy)ethyl]urea by the procedure described in Example 18) in 600 ml of 3:1 ether-pentane is stirred with 200 ml each of ether and methanol at 0°C. 14 g of 11β,16α,17,21-tetrahydroxypregna-1,4-diene-3,20-dione, 16,17-cycloborate is added in portions. After nitrogen evolution ceases the solvents are removed in vacuo and the residue is dissolved in chloroform and chromatographed on a 150 g-silica gel column. Elution with chloroform and then 1:1 chloroform-ethyl acetate gives 4.0 g of TLC pure 16α-[2-(tetrahydropyran-2-yloxy)ethoxy]11β,17,21-trihydroxypregna-1,4-diene-3,20-dione.

B.

16α-[2-(Tetrahydropyran-2-yloxy)ethoxy]-11β,17,21-trihydroxypregna-1,4-diene-3,20-dione, 21-acetate A solution of 3.75 g of 16α-[2-tetrahydropyran-2-yloxy)ethoxy]-11β,17,21-trihydroxypregna-1,4-diene-3,20-dione in 15 ml of pyridine and 5 ml of acetic anhydride is kept at room temperature for 4 hours and the solvents are then evaporated in vacuo. The residue is dissolved in chloroform and washed with dilute hydrochloric acid, water, dilute sodium bicarbonate solution, and dried. Solvent removal gives 4.9 g of crude 16α-[2-(tetrahydropryan-2-yloxy)ethoxy]-11β,17,21-trihydroxypregna-1,4-diene-3,20-dione, 21-acetate.

C.

16α-(2-Hydroxyethoxy)-11β,17,21-trihydroxypregna-1,4-diene-3,20-dione, 21-acetate A solution of 4.9 g of crude 16α-[2(tetrahydropyran-2-yloxy)ethoxy]-11β,17,21-trihydroxypregna-1,4-diene-3,2-dione, 21-acetate in 60 ml each of acetic acid and water is stirred for 6 hours at room temperature. The solvents are removed in vacuo and the residue is dissolved in chloroform and washed with 5% sodium bicarbonate solution and dried. Solvent removal gives 3.9 g of product which is combined with 750 mg of product from a different batch and chromatographed on a 90 g-silica gel column. Elution with chloroform and then 1:1 chloroform-ethyl acetate gives 3.7 g of material which crystallizes from acetone-hexane to give 3.17 of 16α-(2-hydroxyethoxy)-11β,17,21-trihydroxypregna-1,4-diene-3,20-dione, 21-acetate, melting point 138°–140°C.

D.

16α-(2-Mesyloxyethoxy)-11β,17,21-trihydroxypregna-1,4-diene-3,20-dione, 21-acetate A solution of 3.0 g of 16α-(2-hydroxyethoxy)-11β,-17,21-trihydroxypregna-1,4-diene-3,20-dione, 21-acetate in 15 ml of pyridine is stirred with 0.75 ml of methane sulfonyl chloride at 0°C for 150 minutes. The mixture is poured into 1.5 liter of cold 1N hydrochloric acid, stirred for a short time, and filtered. The resulting solid is dissolved in chloroform, washed with water, dried, and evaporated in vacuo to give 4.0 g of crude 16α-(2-mesyloxyethoxy)-11β,17,21-trihydroxypregna-1,4-diene-3,20-dione, 21-acetate

E.

11β,21-Dihydroxypregna-1,4-dieno[16α,17-b][1,4]-dioxane-3,20-dione, 21-acetate

A solution of 4.0 g of crude 16α-(2-mesyloxyethoxy)-11β,17,21-trihydroxypregna-1,4-diene-3,20-dione, 21-acetate in 200 ml of dimethylsulfoxide is stirred at 110°C under nitrogen, with 4.0 g of sodium bicarbonate for 2 hours. The slurry is cooled, poured into 2 liters of cold 2.5% hydrochloric acid, and extracted with chloroform (three 250 ml portions). The chloroform solution is washed with two 1 liter portions of 2.5% hydrochloric acid, dried, and evaporated in vacuo. The residue is dissolved in chloroform and chromatographed on a 66 g-silica gel column. Elution with chloroform gives 2.4 g of material which crystallizes from acetone-hexane to give 1.55 g of 11β,21-dihydroxypregna-1,4-dieno[16α,-17-b][1,4]dioxane-3,20-dione, 21-acetate, melting point 280°–282°C.

EXAMPLES 23–25

Following the procedure of Example 1, but substituting the steroid listed in column I for 9-fluoro-11β, 16α,17,21-tetrahydroxypregn-4-ene-3,20-dione, 16,17-cycloborate, the steroid listed in column II is obtained.

| Example | Column I | Column II |
| --- | --- | --- |
| 23 | 9-chloro-16α,17,21-trihydroxy-pregn-4-ene-3,11,20-trione, 16,17-cycloborate | 9-chloro-5'ϵ,21-dihydroxypregn-4-eno[16α,17-b][1,4]dioxane, 3,11,20-trione, 21-acetate |
| 24 | 9-bromo-6α-methyl-11β,16α,17,21-tetrahydroxypregn-4-ene-3,20-dione, 16,17-cycloborate | 9-bromo-6α-methyl-5'ϵ,11β,21-trihydroxypregn-4-eno[16α,17-b][1,4]-dioxane-3,20-dione, 21-acetate |
| 25 | 2α-methyl-11β,16α,17,21-tetrahydroxypregn-4-ene-3,20-dione, 16,17-cycloborate | 2α-methyl-5'ϵ,11β,21-trihydroxypregn-4-eno[16α,17-b][1,4]-dioxane-3,20-dione, 21-acetate |

EXAMPLES 26–28

Following the procedure of Example 15, but substituting the acid anhydride listed in column I for acetic anhydride, the steroid listed in column II is obtained.

| Example | Column I | Column II |
| --- | --- | --- |
| 26 | benzoic anhydride | 21-chloro-9-fluoro-5'ε,11β-dihydroxypregna-1,4-dieno[16α,17-b][1,4]dioxane-3,20-dione, 5'-benzoate |
| 27 | cyclohexanecarboxylic anhydride | 21-chloro-9-fluoro-5'ε,11β-dihydroxypregna-1,4-dieno[16α,17-b][1,4]dioxane-3,20-dione, 5'-cyclohexanecarboxylate |
| 28 | o-bromobenzoic anhydride | 21-chloro-9-fluoro-5'ε,11β-dihydroxypregna-1,4-dieno[16α,17-b][1,4]dioxane-3,20-dione, 5'-o-bromobenzoate |

EXAMPLES 29–32

Following the procedure of Example 20, but substituting the steroid listed in column I for 21-chloro-9-fluoro-11β,16α,17-trihydroxypregna-1,4-diene-3,20-dione, 16,17-cycloborate, the steroid listed in column II is obtained

| Example | Column I | Column II |
| --- | --- | --- |
| 29 | 9-fluoro-11β,16α,17-trihydroxypregna-1,4-diene-3,20-dione, 16,17-cycloborate | 9-fluoro-2',3'-dihydro-11β-hydroxy-5'-phenylpregna-1,4-dieno[16α17-b]-[1,4]dioxin-3,20-dione |
| 30 | 9,21-difluoro-11β,16α,17-trihydroxypregna-1,4-diene-3,20-dione, 16,17-cycloborate | 9,21-difluoro-2',3'-dihydro-11β-hydroxy-5'-phenylpregna-1,4-dieno[16α,17-b]-[1,4]dioxin-3,20-dione |
| 31 | 11β,16α,17-trihydroxypregna-1,4-diene-3,20-dione, 16,17-cycloborate | 2',3'-dihydro-11β-hydroxy-5'-phenylpregna-1,4-dieno[16α,17-b][1,4]-dioxin-3,20-dione |
| 32 | 21-bromo-9-fluoro-11β,16α,17-trihydroxypregna-1,4-diene-3,20-dione, 16,17-cycloborate | 21-bromo-9-fluoro-2',3'-dihydro-11β-hydroxy-5'-phenylpregna-1,4-dieno-[16α,17-b][1,4]dioxin-3,20-dione |

EXAMPLES 33–35

Following the procedure of Example 22, but substituting the acid anhydride listed in column I for acetic anhydride, the steroid listed in column II is obtained.

| Example | Column I | Column II |
| --- | --- | --- |
| 33 | valeric anhydride | 11β,21-dihydroxypregna-1,4-dieno[16α,17-b]-[1,4]dioxane-3,20-dione, 21-valerate |
| 34 | benzoic anhydride | 11β,21-dihydroxypregna-1,4-dieno[16α,17-b]-[1,4]dioxane-3,20-dione, 21-benzoate |
| 35 | p-toluic anhydride | 11β,21-dihydroxypregna-1,4-dieno[16α,17-b]-[1,4]dioxane-3,20-dione, 21-toluate |

EXAMPLE 36

21-Chloro-5'-(4-chlorophenyl)-9-fluoro-2',3'-dihydro-11β-hydroxypregna-1,4-dieno[16α,17-b]-[1,4]dioxin-3,20-dione Following the procedure of Example 20, but substituting 2-(4-chlorophenyl)-3-diazo-1-propene for 2-phenyl-3-diazo-1-propene, yields 21-chloro-5'-(4-chlorophenyl)-9-fluoro-2',3'-dihydro-11β-hydroxypregna-1,4-dieno[16α,17-b][1,4]dioxin-3,20-dione, melting point 212°–214°C, dec., softening at 200°C.

EXAMPLE 37

21-Chloro-5'-(1,1-dimethylethyl)-9-fluoro-2',3'-dihydro-11β-hydroxypregna-1,4-dieno[16α,17-b]-[1,4]dioxin-3,20-dione Following the procedure of Example 7, but substituting 2-(1,1-dimethylethyl)-3-diazo-1-propene for 2-methyl-3-diazo-1-propene, yields 21-chloro-5'-(1,1-dimethylethyl)-9-fluoro-2',3'-dihydro-11β-hydroxypregna-1,4-dieno-[16α,17-b][1,4]dioxin-3,20-dione, melting point 240°–242°C, dec.

EXAMPLE 38

9-Fluoro-11β,21-dihydroxy-5'ξ-methylpregn-4-eno-[16α,17-b][1,4]dioxane-3,20-dione, 21-acetate 9-Fluoro-11β, 17,21-trihydroxy-16α-(2ξ-hydroxypropoxy)pregn-4-ene-3,20-dione, 21-acetate A solution of 1.0 g of 9-fluoro-11β, 17,21-trihydroxy-16α-(2-oxopropoxy)pregn-4-ene-3,20-dione, 21-acetate (prepared as described in Example 2D) in 80 ml of methanol is cooled to 0°C and 80 mg of sodium borohydride is added. After 10 minutes the solution is poured into chloroform and extracted with dilute hydrochloric acid. The chloroform solution is dried and evaporated in vacuo to give the crude product. Chromatography on a 30 g-silica gel column, eluting with 9:1 chloroform-ethyl acetate, yields 730 mg of the title compound.

B. 9-Fluoro-11β, 17,21-trihydroxy-16α-(2ξ-mesyloxypropoxy)pregn-4-ene-3,20-dione, 21-acetate A solution of 700 mg of 9-fluoro-11β, 17,21-trihydroxy-16α-(2ξ-hydroxypropoxy)pregn-4-ene-3,20-dione, 21-acetate in 10 ml of pyridine is cooled to 0°C and 0.4 ml of methanesulfonyl chloride is added. After 4 hours the mixture is extracted, dried and evaporated to give the title compound.

C. 9-Fluoro-11β, 21-dihydroxy-5′ξ-methylpregn-4-eno-[16α,17-b][1,4]dioxane-3,20-dione, 21-acetate A solution of 750 mg of 9-fluoro-11β, 17,21-trihydroxy-16α-(2ξ-mesyloxypropoxy)pregn-4-ene-3,20-dione, 21-acetate in 50 ml of dimethylsulfoxide is stirred at 110°C under nitrogen with 1.0 g of sodium bicarbonate. After 2 hours the reaction mixture is extracted, dried and evaporated to yield the title compound.

EXAMPLE 39

9-Fluoro-11β, 21-dihydroxy-5′ξ-phenylpregn-4-eno-[16α,17-b][1,4]dioxane-3,20-dione, 21-acetate

A. 9-Fluoro-11β, 17,21-trihydroxy-16α-(2-phenyl-2-hydroxyethoxy)-pregn-4-ene-3,20-dione, 21-acetate A solution of 1.0 g of 9-fluoro-11β, 17,21-trihydroxy-16α-(2-phenyl-2-oxoethoxy)pregn-4-ene-3,20-dione, 21-acetate (prepared as described in Example 4D) in 80 ml of methanol is cooled to 0°C and 80 mg of sodium borohydride is added. After 10 minutes, the solution is poured into chloroform and extracted with dilute hydrochloric acid. The chloroform solution is dried and evaporated in vacuo to yield the title compound.

B. 9-Fluoro-11β, 17,21-trihydroxy-16α-(2-mesyloxy-2-phenylethoxy)-pregn-4-ene-3,20-dione, 21-acetate A solution of 700 mg of 9-fluoro-11β,17,21-trihydroxy-16α-(2-phenyl-2-hydroxyethoxy)pregn-4-ene-3,20-dione, 21-acetate in 10 ml of pyridine is cooled to 0°C and 0.4 ml of methanesulfonyl chloride is added. After 4 hours the mixture is extracted, dried and evaporated to give the title compound.

C. 9-Fluoro-11β, 21-dihydroxy-5′ξ-phenylpregn-4-eno-[16α,17-b][1,4]dioxane-3,20-dione, 21-acetate A solution of 750 mg of 9-fluoro-11β,17,21-trihydroxy-16α-(2-mesyloxy-2-phenylethoxy)pregn-4-ene-3,20-dione, 21-acetate in 50 ml of dimethylsulfoxide is stirred at 110°C under nitrogen with 1.0 g of sodium bicarbonate. After 2 hours the reaction mixture is extracted, dried and evaporated to yield the title compound.

EXAMPLE 40

21-Chloro-9-fluoro-11β-hydroxy-4′-methyl-5′-phenyl-pregna-1,4-dieno[16α,17-b][1,4]dioxin-3,20-dione

A. 21-Chloro-9-fluoro-11β, 17-dihydroxy-16α-[(3-oxo-3-phenylprop-2-yl)oxy]-pregna-1,4-diene-3,20-dione a. N-[2-(3-oxo-3-phenylpropyl)]phthalimide A solution of 58 g of α-bromopropionphenone and 50 g of potassium phthalimide in 200 ml of dimethylformamide is refluxed for 2 hours under nitrogen, cooled, and poured into 500 ml of water. The resulting mixture is extracted with ether, and the ether solution is dried and evaporated in vacuo. A solution of the residue in 200 ml of ether gives the title compound as a solid.

b. 2-[1-(N-phthalimidoethyl)]-2-phenyldioxolane

A solution of 49.9 g of N-[2-(3-oxo-3-phenylpropyl)]-phthalimide in 500 ml of toluene is refluxed for a total of 13 days with 5 g of p-toluenesulfonic acid and 150 ml of ethylene glycol. The solution is cooled, diluted with chloroform, and washed with dilute sodium bicarbonate solution. The chloroform solution is dried and evaporated to give, on trituration with ether, 51.5 g of the title compound, melting point 127°-130°C.

c. 2-(1-Aminoethyl)-2-phenyldioxolane

A solution of 51.5 g of 2-[1-(N-phthalimidoethyl)]-2-phenyldioxolane in 500 ml of methanol is refluxed for 6 hours with 5.76 g of hydrazine. The slurry is cooled, filtered and the solid washed well with methanol. The filtrate is evaporated in vacuo, and the residue triturated with dichloromethane and filtered. The filtrate is distilled in vacuo to give 28.25 g of the title compound, boiling point 97°-100°C at 1.1 mm Hg.

d. 2-Phenyl-2-(1-ethoxycarbonylaminoethyl)-dioxolane

A solution of 2-(1-aminoethyl)-2-phenyldioxolane (20 mmoles), triethylamine (24 mmoles), and ethyl chloroformate (22 (mmoles) in 100 ml of dichloromethane is stirred at 0°C for 2 hours, washed with water, dried, and evaporated to give the title compound.

e. 2-Phenyl-2-(1-diazoethyl)dioxolane

Following the procedure of Example 4A (parts c and d), but substituting 2-phenyl-2-(1-ethoxycarbonylaminoethyl)dioxolane for N-(2-phenyl-2-propenyl)ethyl carbamate, the title compound is obtained.

f. 21-Chloro-9-fluoro-11β,17-dihydroxy-16α-[(3-oxo-3-phenylprop-2-yl)oxy]pregna-1,4-diene-3,20-dione A solution of 2-phenyl-2-(1-diazoethyl)dioxolane in 3:2 ether-pentane is diluted with methanol and cooled to 0°C. 21-Chloro-9-fluoro-11β,16α,17-trihydroxypregna-1,4-diene-3,20-dione, 16,17-cycloborate is added in portions until nitrogen evolution ceases. The solvent is removed in vacuo.

The residue is purified and dissolved in tetrahydrofuran. The solution is refluxed with hydrochloric acid. The solvent is removed in vacuo and the residue is diluted with water, extracted with chloroform, and the chloroform solution is washed with 5% sodium bicarbonate solution, water, dried, and evaporated to yield the title compound.

B. 21-Chloro-9-fluoro-11β-hydroxy-4′-methyl-5′-phenylpregna-1,4-dieno[16α,17-b][1,4]dioxin-3,20-dione A slurry of 150 mg of p-toluenesulfonic acid in 750 ml of benzene is refluxed with a Dean-Stark trap. The first 150 ml of benzene-water azeotrope is discarded and Linde type 4A molecular sieves are added to the trap. After 30 minutes at reflux, the solution is cooled and 1.0 g of 21-chloro-9-fluoro-11β,17-dihydroxy-16α-[3-oxo-3-phenylprop-2-yl)oxy]pregna-1,4-diene-3,20-dione is added. The mixture is refluxed for 6 hours under nitrogen, cooled, washed with 5% sodium bicarbonate solution, water, dried and evaporated in vacuo to yield the title compound.

What is claimed is:

1. A 3,20-diketo pregnene having an 11β-hydroxy group or an 11-keto group and having fused on the 16 and 17 positions a 1,4-dioxane ring or a 1,4-dioxin ring.

2. A steroid in accordance with claim 1 having fused on the 16 and 17 positions a 1,4-dioxane ring.

3. A steroid in accordance with claim 1 having fused on the 16 and 17 positions a 1,4-dioxin ring.

4. A steroid in accordance with claim 1 wherein the fused 1,4-dioxane ring or 1,4-dioxin ring has the structural formula

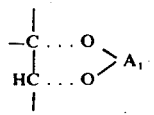

wherein $A_1$ is

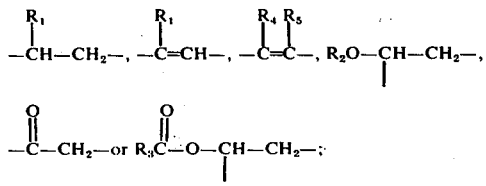

wherein $R_1$ is hydrogen, alkyl or aryl; $R_2$ is hydrogen, alkyl or arylalkyl; $R_3$ is alkyl, cycloalkyl or aryl; and $R_4$ and $R_5$ are the same or different and are alkyl or aryl.

5. A steroid in accordance with claim 4 wherein $A_1$ is —$CH_2$—$_{CH2}$—,

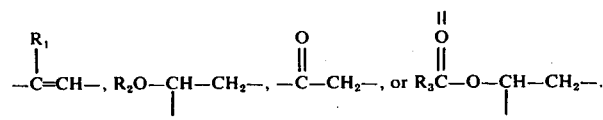

6. A steroid having the formula

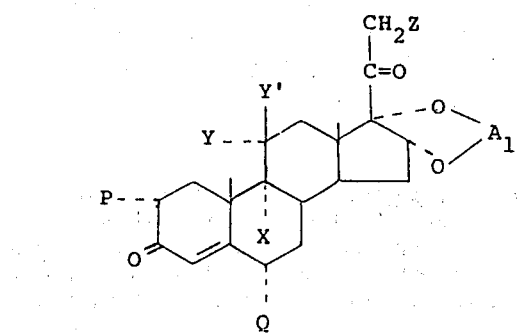

and the 1,2-dehydro and 6,7-dehydro derivatives thereof, wherein Z is hydrogen, hydroxyl, acyloxy or halogen; Y is hydrogen and Y' is hydroxyl or together Y and Y' are =O; X is hydrogen or halogen; P is hydrogen, methyl or chloro; Q is hydrogen, methyl or fluoro; $A_1$ is

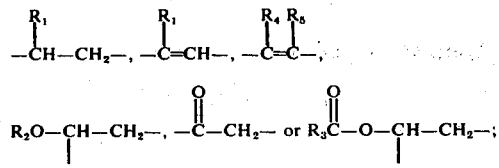

$R_1$ is hydrogen, alkyl or aryl; $R_2$ is hydrogen, alkyl or arylalkyl; $R_3$ is alkyl, cycloalkyl or aryl; and $R_4$ and $R_5$ are the same or different and are alkyl or aryl.

7. A steroid in accordance with claim 6 wherein $A_1$ is

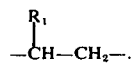

8. A steroid in accordance with claim 6 wherein $A_1$ is

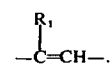

9. A steroid in accordance with claim 6 wherein $A_1$ is

10. A steroid in accordance with claim 6 wherein $A_1$ is

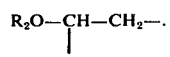

11. A steroid in accordance with claim 6 wherein $A_1$ is

12. A steroid in accordance with claim 6 wherein $A_1$ is

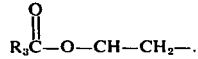

13. A steroid in accordance with claim 6 wherein X is fluoro.

14. A steroid in accordance with claim 6 wherein Z is hydroxyl.

15. A steroid in accordance with claim 6 wherein Z is acyloxy.

16. A steroid in accordance with claim 6 wherein Z is halogen.

17. A steroid in accordance with claim 6 wherein Z is chlorine.

18. A steroid in accordance with claim 6 having the name 9-fluoro-5'ξ,11β,21-trihydroxypregn-4-eno-]16α,17-b][1,4]dioxane-3,20-dione, 21-acetate.

19. A steroid in accordance with claim 6 having the name 9-fluoro-2',3'-dihydro-11β,21-dihydroxy-5'-methylpregn-4-eno[16α,17-b][1,4]dioxin-3,20-dione, 21-acetate.

20. A steroid in accordance with claim 6 having the name 9-fluoro-2',3'-dihydro-11β,21-dihydroxypregn-4-eno[16α,17-b][1,4]dioxin-3,20-dione.

21. A steroid in accordance with claim 6 having the name 21-chloro-9-fluoro-2',3'-dihydro-11β-hydroxy-5'-methylpregna-1,4-dieno[16α,17-b][1,4]dioxin-3,20-dione.

22. A steroid in accordance with claim 6 having the name 5'ξ-ethoxy-9-fluoro-11β,21-dihydroxypregn-4-eno-[16α,17-b][1,4]dioxane-3,20-dione.

23. A steroid in accordance with claim 6 having the name 21-chloro-5'ξ-ethoxy-9-fluoro-11β-hydroxypregn-4-eno[16α,17-b][1,4]dioxane-3,20-dione.

24. A steroid in accordance with claim 6 having the name 9-fluoro-5'ξ,11β,21-trihydroxypregn-4-eno-[16α,17-b][1,4]dioxane-3,20-dione.

25. A steroid in accordance with claim 6 having the name 9-fluoro-5'ξ,11β,21-trihydroxypregn-4-eno-[16α,17-b][1,4]dioxane-3,20-dione, 5',21-diacetate.

26. A steroid in accordance with claim 6 having the name 21-chloro-9-fluoro-5'ξ,11α-dihydroxypregna-1,4-dieno[16α,17-b][1,4]dioxane-3,20-dione.

27. A steroid in accordance with claim 6 having the name 21-chloro-9-fluoro-5'ξ,11β-dihydroxypregna-1,4-dieno[16α,17-b][1,4]dioxane-3,20-dione, 5'-acetate.

28. A steroid in accordance with claim 6 having the name 21-chloro-9-fluoro-2',3'-dihydro-11β-hydroxypregna-1,4-dieno[16α,17-b][1,4]dioxin-3,20-dione.

29. A steroid in accordance with claim 6 having the name 9-fluoro-11β, 21-dihydroxypregn-4-eno[16α,17-b]-[1,4]dioxane-3,5',20-trione, 21-acetate.

30. A steroid in accordance with claim 6 having the name 21-chloro-9-fluoro-2',3'-dihydro-11β-hydroxy-5'-phenylpregna-1,4-dieno[16α,17-b][1,4]dioxin-3,20-dione.

-dieno-[A steroid in accordance with claim 6 having the name 21-chloro-9-fluoro-11β-hydroxypregna-1,4-dieno[16α,17-b][1,4]dioxane-3,20-dione.

32. A steroid in accordance with claim 6 having the name 11β, 21-dihydroxypregna-1,4-dieno[16α,17-b][1,4]-dioxane-3,20-dione, 21-acetate.

33. A steroid in accordance with claim 6 having the name 21-chloro-5'-(4-chlorophenyl)-9-fluoro-2',3'-dihydro-11β-hydroxypregna-1,4-dieno[16α,17-b][1,4]dioxin-3,20-dione.

34. A steroid in accordance with claim 6 having the name 21-chloro-5'-(1,1-dimethylethyl)-9-fluoro-2',3'-dihydro-11β-hydroxypregna-1,4-dieno[16α,17-b][1,4]dioxin-3,20-dione.

35. A steroid having the formula

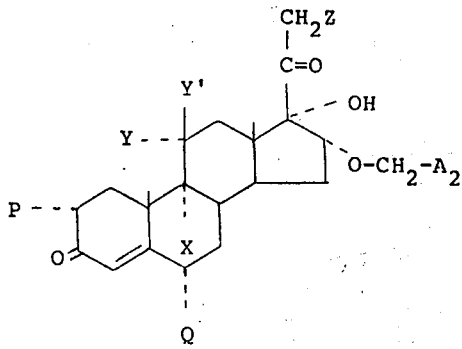

and the 1,2-dehydro and 6,7-dehydro derivatives thereof, wherein Z is hydrogen, hydroxyl, acyloxy or halogen: Y is hydrogen and Y' is hydroxyl, or together Y and Y' are =O; X is hydrogen or halogen; P is hydrogen, methyl or chloro; Q is hydrogen, methyl or fluoro; and $A_2$ is

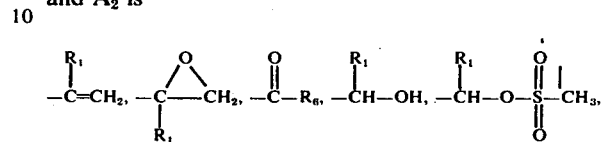

$-CH(O-R_7)_2$, or

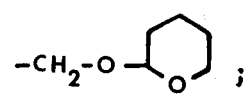

$R_1$ is hydrogen, alkyl or aryl; $R_6$ is alkyl or aryl; $R_7$ is alkyl or arylalkyl.

36. A steroid having the formula

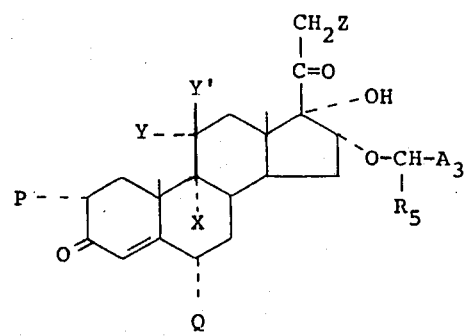

and the 1,2-dehydro and 6,7-dehydro derivatives thereof, wherein Z is hydrogen, hydroxyl, acyloxy or halogen; Y is hydrogen and Y' is hydroxyl, or together Y and Y' are =O; X is hydrogen or halogen; P is hydrogen, methyl, or chloro; Q is hydrogen, methyl or fluoro; $A_3$ is

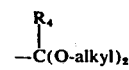

or

and $R_4$ and $R_5$ are the same or different and are alkyl or aryl.

* * * * *

UNITED STATES PATENT AND TRADEMARK OFFICE
CERTIFICATE OF CORRECTION

PATENT NO. : 3,971,772
DATED : July 27, 1976
INVENTOR(S) : Christopher M. Cimarusti et al.

It is certified that error appears in the above-identified patent and that said Letters Patent are hereby corrected as shown below:

Column 8, line 3, "80 C to 110 C" should read --80°C to 110°C--.
Column 8, line 23, "10 C to 20 C" should read --10°C to 20°C--.
Column 8, line 24, "0 C" should read --0°C--.
Column 8, line 47, "10 C to 40 C" should read --10°C to 40°C--.
Column 8, line 48, "0 C" should read --0°C--.
Column 8, line 51, "[16 ,17-b]" should read --[16α,17-b]--.
Column 8, line 67, "60 C to 130 C" should read --60°C to 130°C--.
Column 9, line 6, should read:

Column 9, line 18, should read:

XV
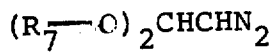

Column 13, line 27, "dichloroemthane" should read --dichloromethane--.
Column 15, line 8, "$C_{27}H_{37}FO_7$:" should read --$C_{27}H_{37}FO_8$:--.

Column 16, line 9, "dihydroxy-P5'-" should read --dihydroxy-5'- --.

Column 20, line 40, the letter "E" should be before the title of the example.
Column 22, line 49, "acetone-lexane" should read --acetone-hexane--.
Column 23, line 11, "11β11β,21-" should read --11β,21- --.
Column 39, line 37, "-dieno-[" should read -- 31. --

Signed and Sealed this

Thirtieth Day of November 1976

[SEAL]

Attest:

RUTH C. MASON
Attesting Officer

C. MARSHALL DANN
Commissioner of Patents and Trademarks